(12) United States Patent
Lintell

(10) Patent No.: US 7,233,228 B2
(45) Date of Patent: Jun. 19, 2007

(54) ALERTING SYSTEM

(75) Inventor: Daniel Thomas de Sausmarez Lintell, Ware (GB)

(73) Assignee: Glaxo Group Limited, Greenford (GB)

( * ) Notice: Subject to any disclaimer, the term of this patent is extended or adjusted under 35 U.S.C. 154(b) by 232 days.

(21) Appl. No.: 10/514,260

(22) PCT Filed: Apr. 25, 2003

(86) PCT No.: PCT/EP03/04406

§ 371 (c)(1),
(2), (4) Date: Oct. 29, 2004

(87) PCT Pub. No.: WO03/092576

PCT Pub. Date: Nov. 13, 2003

(65) Prior Publication Data
US 2005/0174216 A1    Aug. 11, 2005

(30) Foreign Application Priority Data
Apr. 29, 2002    (GB) ................................. 0209782.2

(51) Int. Cl.
G08B 1/00    (2006.01)
G08B 47/00    (2006.01)

(52) U.S. Cl. ............................. 340/309.7; 340/309.4; 368/10; 221/8

(58) Field of Classification Search ............ 340/309.4, 340/309.7, 309.16; 368/10; 221/3, 8
See application file for complete search history.

(56) References Cited

U.S. PATENT DOCUMENTS

| | | | |
|---|---|---|---|
| 4,223,801 A | 9/1980 | Carlson | 221/3 |
| 4,419,016 A | 12/1983 | Zoltan | 368/10 |
| 4,588,303 A | 5/1986 | Wirtschafter et al. | 368/10 |
| 5,363,842 A | 11/1994 | Lanpher et al. | 128/200.14 |
| 5,392,952 A * | 2/1995 | Bowden | 221/3 |
| 5,408,443 A | 4/1995 | Weinberger | 368/10 |
| 5,412,372 A | 5/1995 | Parkhurst et al. | 340/568.1 |
| 5,505,195 A | 4/1996 | Sallis et al. | 128/203.15 |
| 5,583,832 A | 12/1996 | DePonty | 368/10 |
| 5,809,997 A | 9/1998 | Wolf | 128/200.23 |
| 6,012,450 A | 1/2000 | Rubsamen | 128/200.14 |
| 6,014,969 A | 1/2000 | Lloyd et al. | 128/200.14 |
| 6,102,855 A | 8/2000 | Farrage et al. | 600/300 |
| 6,252,494 B1 | 6/2001 | Howell | 340/309.8 |
| 6,529,446 B1 * | 3/2003 | de la Huerga | 368/10 |

FOREIGN PATENT DOCUMENTS

| | | |
|---|---|---|
| EP | 0857456 | 8/1998 |
| EP | 0933092 | 8/1999 |

(Continued)

Primary Examiner—Jeffery Hofsass
Assistant Examiner—Anne V Lai
(74) Attorney, Agent, or Firm—James P. Riek

(57) ABSTRACT

An alerting system for use in generating an alert in respect of usage of a device, the alerting system including a detector capable of detecting an event that is indicative of usage of the device, the alerting system being arranged to invoke a selected alert state prior to the activation of a forthcoming said event by a user, the alert state being selectable from a plurality of different alert states, wherein each of the different alert states represents a different stage of elapsed time since a previous said event, and wherein the alerting system is arranged to select an alert state in dependence on the elapsed time.

24 Claims, 20 Drawing Sheets

FOREIGN PATENT DOCUMENTS

| | | |
|---|---|---|
| EP | 1161933 | 12/2001 |
| WO | WO 99/38556 | 8/1999 |
| WO | WO 99/43284 | 9/1999 |
| WO | WO 00/21598 | 4/2000 |
| WO | WO 01/41845 | 6/2001 |
| WO | WO 01/50434 | 7/2001 |
| WO | WO 01/93801 | 12/2001 |
| WO | WO 02/78593 | 10/2002 |

* cited by examiner

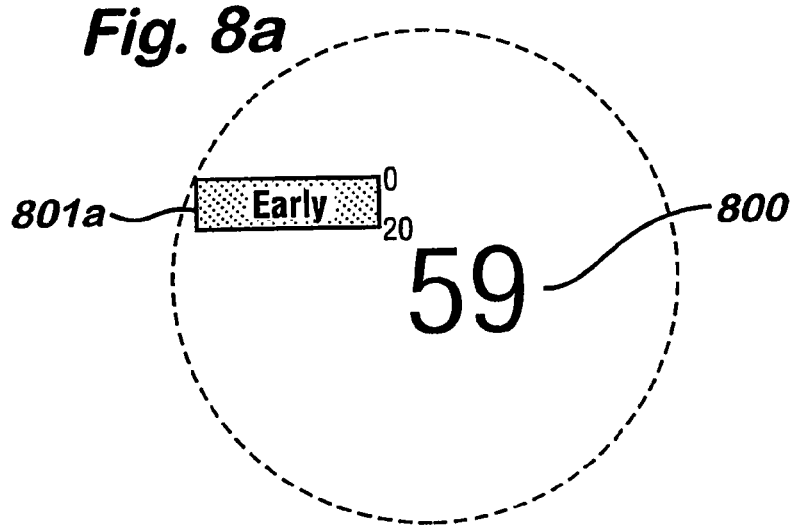
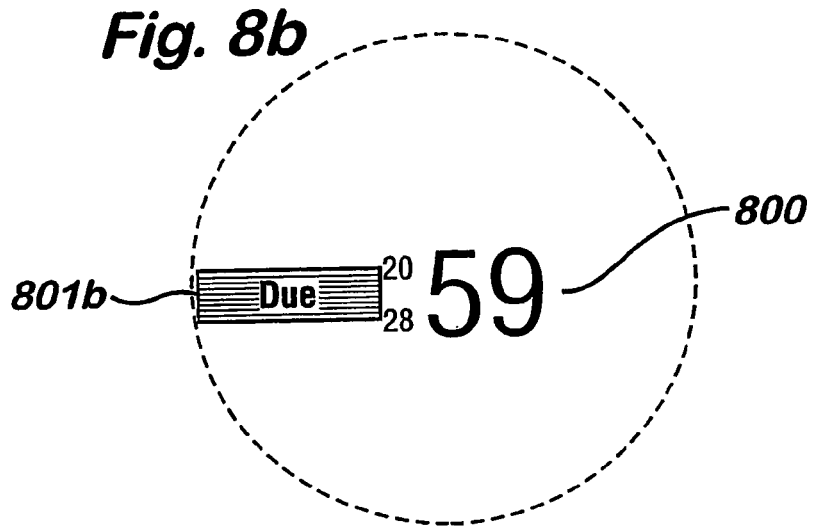
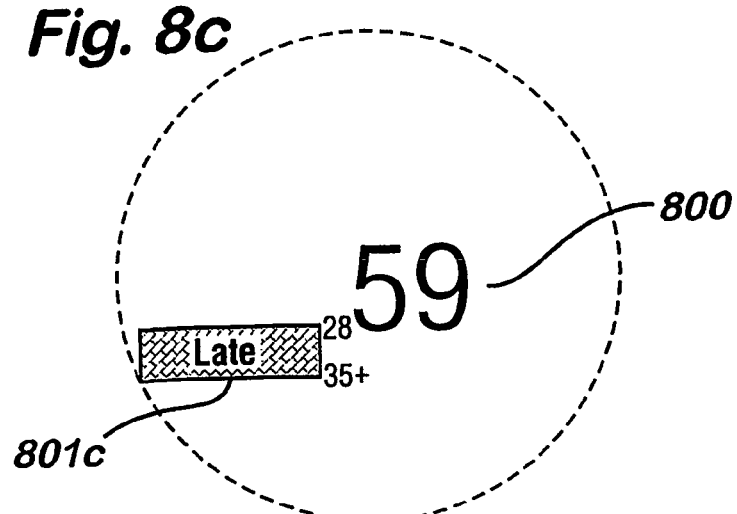

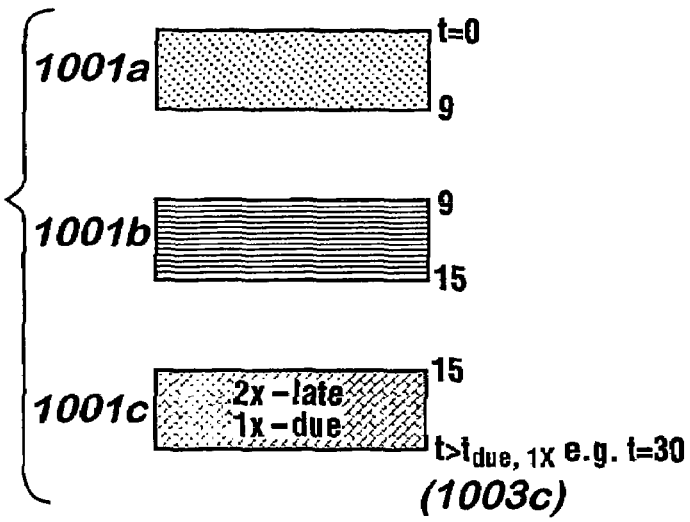
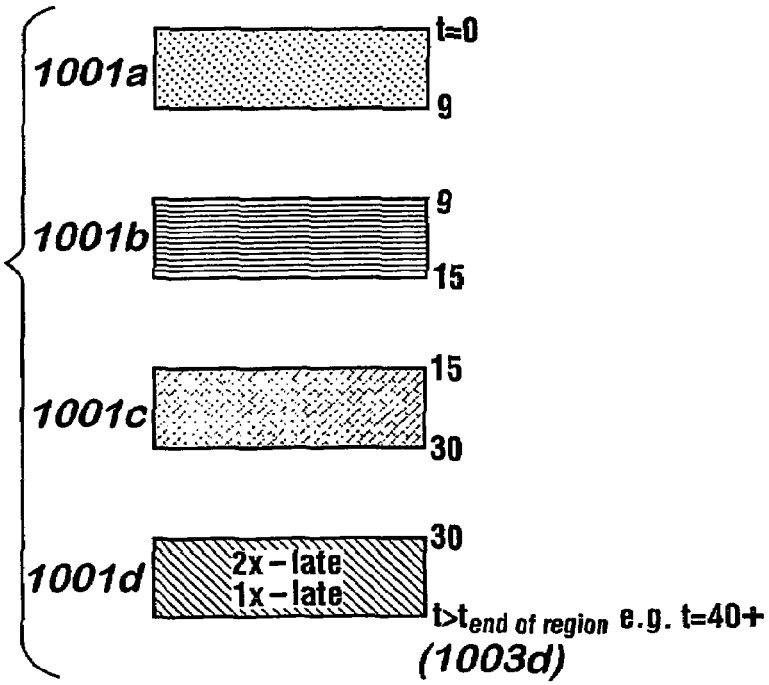

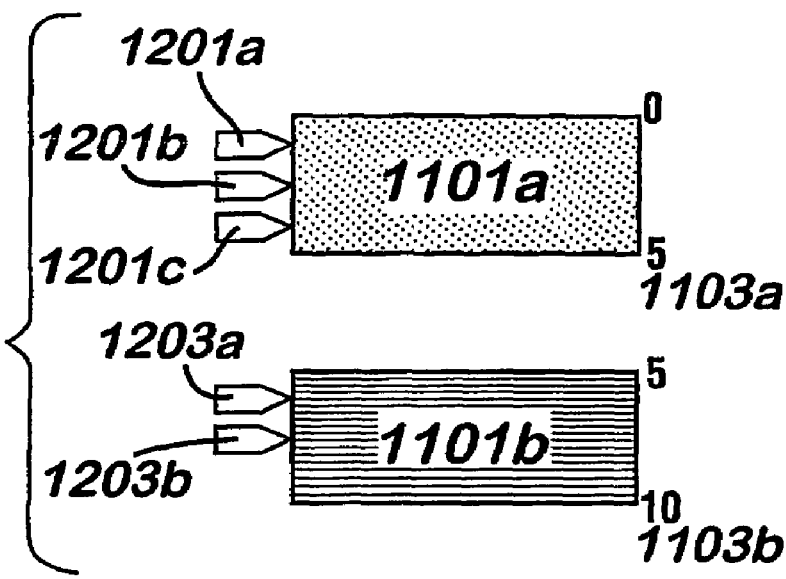
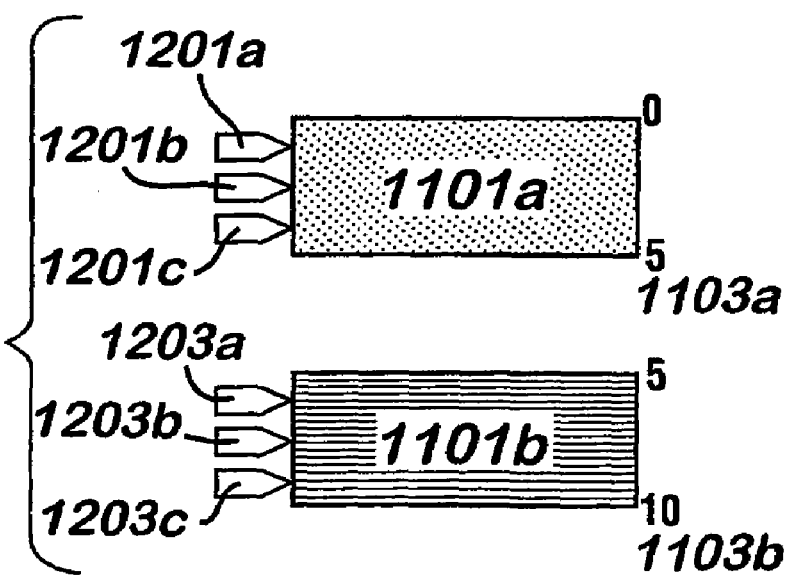

ALERTING SYSTEM

CROSS-REFERENCE TO RELATED APPLICATIONS

This application is filed pursuant to 35 USC 371 as a United States National Phase Application of International Patent Application Serial No. PCT/EP03/04406 filed on 25 Apr. 2003, which claims priority from GB 0209782.2 filed on 29 Apr. 2002 in the United Kingdom.

TECHNICAL FIELD

The present invention relates to an alerting system for use in generating an alert in respect of a forthcoming event. The invention particularly, but not exclusively, relates to an alerting system for use with a medicament dispenser.

BACKGROUND TO THE INVENTION

Many conditions are treated by taking one or more drugs at regular intervals, and the success of the treatment is largely dependent on the ability of the user to comply with the regimen associated with the drug. Management of regimen compliance is assisted by various reminding devices and systems, which either generate an alarm at certain specified times or inform the user whether or not a dose is due in response to a request for medication. For example, U.S. Pat. No. 4,419,016 discloses an alarm system arranged to generate an alert when a next dose is due to be taken and a time keeping system that displays the amount of time since a last dose is deemed to have been taken. The alert is generated on the basis of absolute time, in that, upon reaching a time that a dose is due, an alarm is generated, whilst the time keeping system merely serves to provide information to the user. WO 02/078593 is a development of the system disclosed in U.S. Pat. No. 4,419,016, in that it uses the time that medication was last taken to identify time of next dose, that is to say it has a reminder system based on dose history informing the user whether a dose is due or not in response to a user requesting a dose.

It would be desirable to provide an improved alerting system for use in a medicament dispenser, where the generation of alerts is based on dose history.

SUMMARY OF THE INVENTION

According to one aspect of the present invention, there is provided an alerting system for use in generating an alert in respect of usage of a device, the alerting system including a detector capable of detecting an event that is indicative of usage of the device, the alerting system being arranged to invoke a selected alert state prior to the activation of a forthcoming said event by a user, the alert state being selectable from a plurality of different alert states, wherein each of the different alert states represents a different stage of elapsed time since a previous said event, and wherein the alerting system is arranged to select an alert state in dependence on the elapsed time.

In the context of medicament dispensers, an event indicative of usage of the device can be an event relating to the dispensing of medicament, such as movement of a refill within the medicament dispenser. Accordingly, when the alerting system is implemented in a medicament dispenser, the detector can be provided by a sensor arranged to detect such refill movement.

When incorporated into a medicament dispenser, an alerting system according to the invention allows the user to review the stage of elapsed time since a previous dose—i.e. whether it is too early to take a dose ("early" stage), time to take a dose ("dose due" stage) or whether the dose time has been missed ("late" stage)—before initiating dispensing of the medicament.

Since the alert states are based on the amount of time that has elapsed since medicament was last taken, the compliance of a user with a selected regimen, that is to say correlation between a time that the user is reminded to take a dose and the time that a dose is actually due, can be increased. This provides an improvement over reminders generated at specified times, where a reminder is given irrespective of how appropriate (or otherwise) it is for the user to take a dose at that time, based on the time that a dose was previously taken.

Patients are quite often mobile, and, when a dose falls due, can be some distance (and thus time) away from the location of their drug. For example, a user could be located 2 hours away from his medicine; if he were to receive an alarm in accordance with known systems, he would be unable to take the medicine for at least 2 hours. The present invention provides an improvement over these known systems, since the plurality of alert states correspond to particular stages of elapsed time since the last dose was taken (e.g. "early" "dose due" and "late"). In the context of our user who is located 2 hours from the location of his drug, with a medicament dispenser according to the invention, the user would know whether the current time is "early", "late", etc. and accordingly can ensure that his journey is started in advance of that time. Thus, in comparison with known methods, the user is able to improve the planning of his activities with respect to his dosage regime.

As with all equipment, medicament dispensers equipped with reminder systems can be expected to malfunction at certain times. In the field of medicine, the effects of generating, for example, reminder messages at inappropriate times, can be hazardous and potentially life-threatening. Given the seriousness of these effects, the medicament dispenser according to the invention leaves the decision to take a dose in the hands of the user—i.e. not issuing a single "dose due" instruction—whilst providing useful assistance in the form of a set of alerts. In addition, by providing the user with information relating to the stage since a previously taken dose, the user is better able to judge whether it is appropriate or not to take a dose.

Advantageously at least one alert state represents a length of time in excess of 2 hours, and at least one alert state preferably corresponds to a period that includes an elapsed time of 24 hours. For a once a day regimen, this means that the medicament dispenser includes an alert state corresponding to a "dose due" stage of elapsed time. Preferably at least one alert state corresponds to a period that includes an elapsed time in excess of 24 hours, thereby including an alert state corresponding to a "late" stage of elapsed time in a once a day regimen.

Preferably, the alert states include a first alert state corresponding to a period which includes an elapsed time of 24 hours and a second alert state corresponding to a period which includes an elapsed time of 12 hours. This represents a regimen-neutral reminder system, in so far as there is one alert state corresponding to "dose due" for each of the once and twice a day regimens.

Conveniently at least one alert state represents a different length of time to that represented by at least one of the other alert states or that represented by the other alert state. For example, if an alert state were embodied as a display mode comprising two or more visible regions, the time periods to which the regions correspond could vary; for example, for the case of a twice a day regimen, where a dose falls due every 12 hours, a region corresponding to an "early" stage of elapsed time could correspond to 0–10 hours of elapsed time; a region corresponding to "dose due" stage of elapsed time could correspond to 10–14 hours of elapsed time, and a region corresponding to "late" stage of elapsed time could correspond to 14–20 hours of elapsed time. In this example, the regions correspond, respectively, to 10, 4 and 6 hours. Advantageously, the respective durations of elapsed time can be driven by the type of medicament, since some medicaments can be expected to be more sensitive to deviations from the ideal spacing between doses than others.

Conveniently at least one alert state comprises a plurality of sub-regions, each sub-region representing a proportion of elapsed time within the stage to which the alert state corresponds. This provides an indication of where the currently elapsed time is, in relation to a particular stage of elapsed time, thereby providing the user with more detailed information.

Further features and advantages of the present invention will become apparent from the following description of preferred embodiments of the invention, given by way of example only, made with reference to the accompanying drawings.

BRIEF DESCRIPTION OF THE DRAWINGS

FIGS. 5, 6, 7, 8a–8e, 9a, 9b, 10a–10d, 11a–11e, 12a–12f, 13a–13c, 14c–14e, 15a–15d, 16a–16d illustrate alternative display configurations showing various alert states indicating different stages of elapsed time.

DETAILED DESCRIPTION OF THE DRAWINGS

Figure 1:
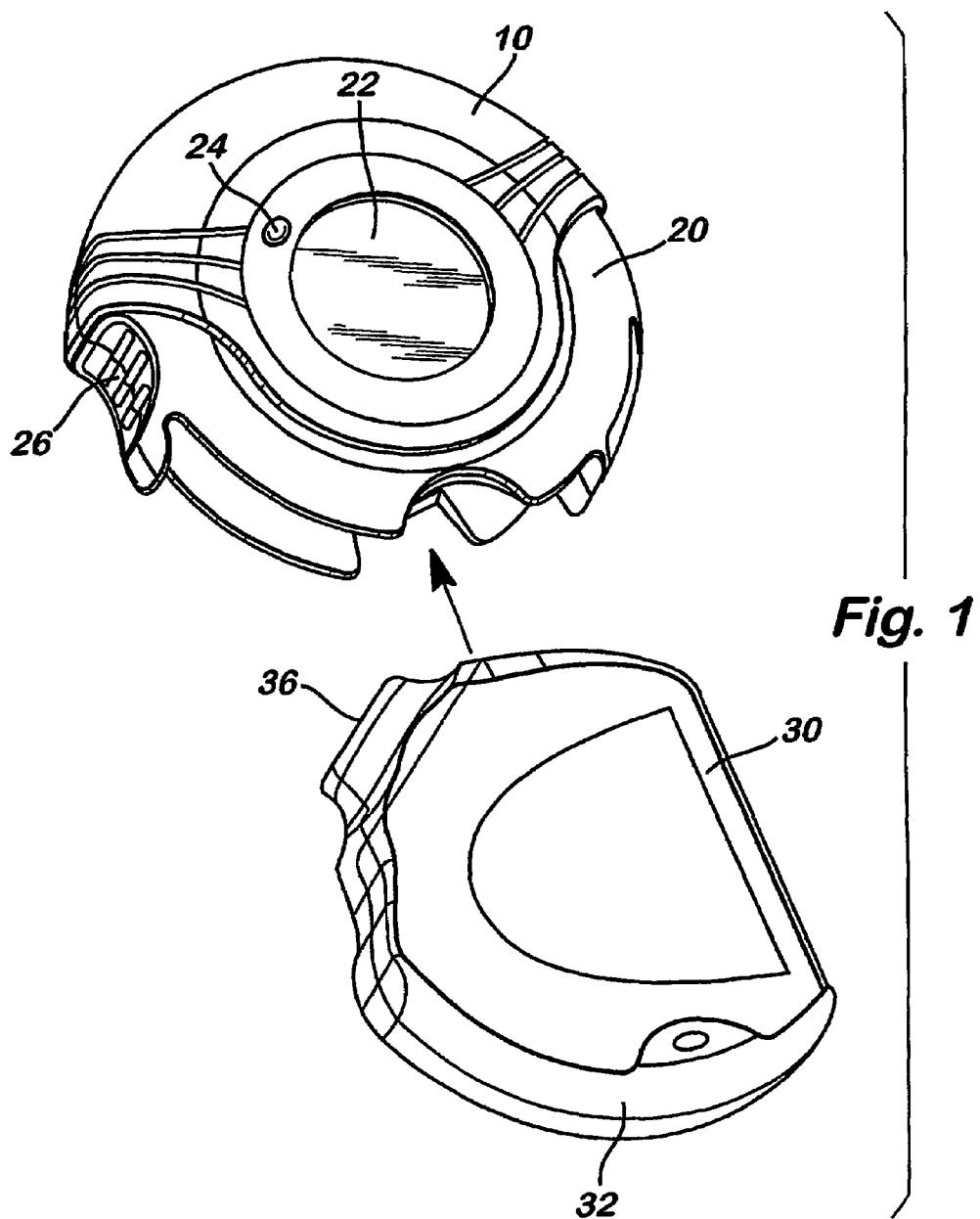
FIG. 1 shows a perspective view of a medicament dispenser within which an embodiment of the invention operates, with the cassette removed from the holder and body.

FIG. 1 shows a medicament dispenser, within which an embodiment of the present invention operates, in the form of a base unit comprising an outer cover 10 and a holder 20, and a refill cassette 30. In this example the medicament dispenser is a dry powder inhaler adapted for oral inhalation. The holder 20, which includes an electronic display 22, is shaped to fit inside cover 10 and is fixed to the body via a bearing (not shown) about which it rotates coaxially. Stops (not shown) protrude from the holder 20 and prevent the holder 20 from rotating more than about 180° relative to the cover 10. The stops also provide two defined positions of the holder 20 within the cover 10. An outer part of the holder is shaped in the form of a concave recess 26 to provide a thumb or finger grip for the user of the device. The holder 20 forms a recess into which the refill cassette 30 latches.

The refill cassette 30 comprises a shell containing the medicament carrier and a mechanism for opening the carrier for the medicament to be accessed. The refill cassette 30 has a rear portion 32 which is exposed by a cut-away part of the holder 20 when the rest of the cassette 30 is contained within the holder 20 so as to allow the cassette to be manually gripped for removal from the holder 20.

The refill cassette 30 also has a mouthpiece 36 from which a user inhales medicament dispensed from the cassette 30.

Figure 2A:
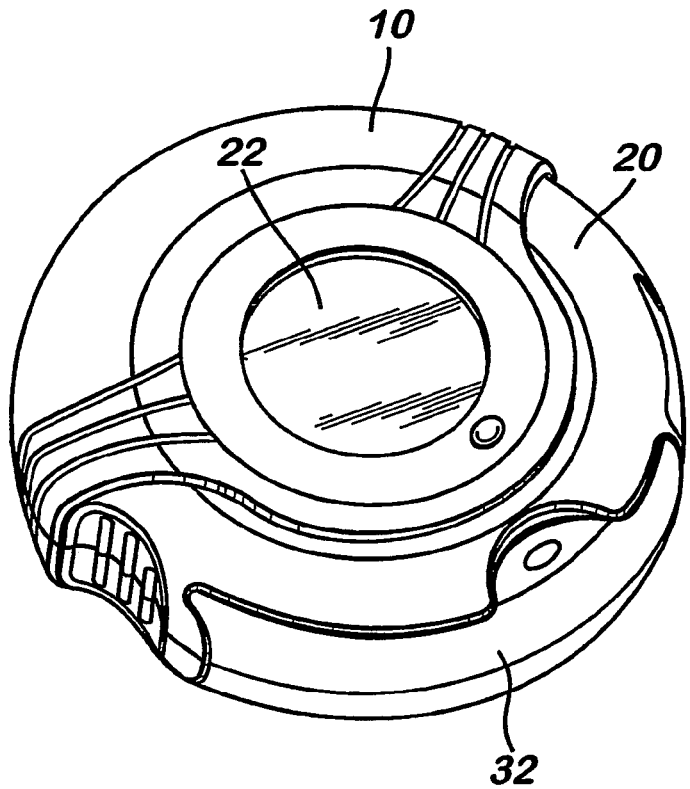
FIG. 2a shows a plan view of the medicament dispenser of FIG. 1 with the cassette in the non-dispensing position.

FIG. 2a shows the medicament dispenser with the cassette 30 in place in the holder 20 and with cover 10 in a non-dispensing position in which the rear end 32 of the cassette is exposed. The cassette 30 is fixed in place by a spring-biased catch (not shown). When the cassette 30 is in the position shown, relative to the holder 20, the cover 10 covers the mouthpiece (not shown). The cover 10 also protects the thumbtab 28 of an indexing lever (not shown) and this prevents accidental indexing of the medicament carrier when the medicament dispenser is not in use.

Figure 2B:
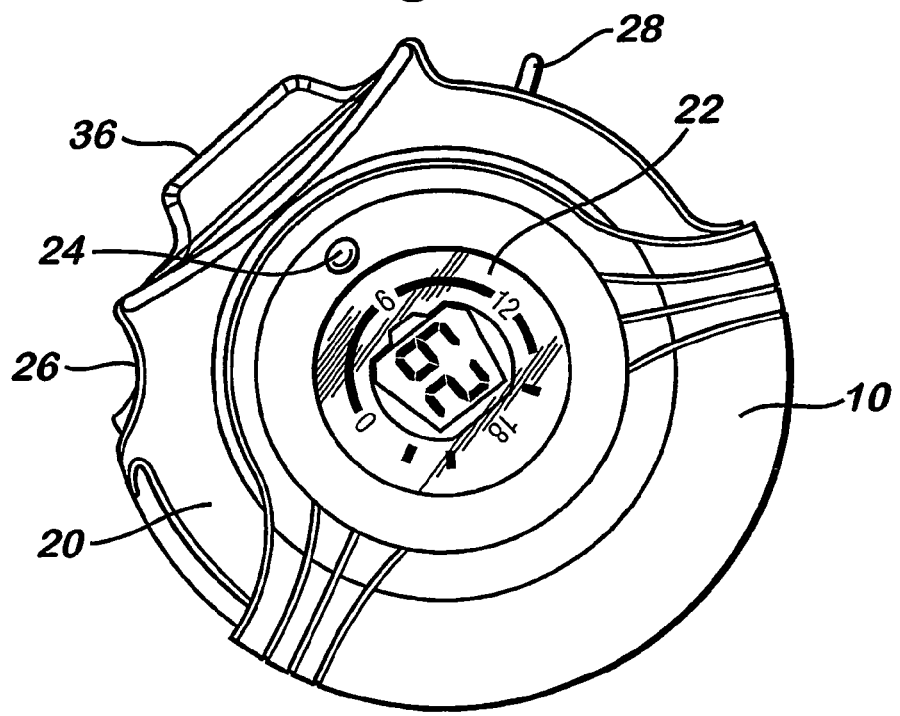
FIG. 2b shows a plan view of the medicament dispenser of FIGS. 1 and 2a with the cassette in the dispensing position.

FIG. 2b shows the medicament dispenser of FIGS. 1 and 2a with the cassette 30 in place in the holder 20 in a dispensing position. The holder 20 has been rotated relative to the cover 10 so that a stop on the holder 20 abuts the cover 10. It can be seen that the holder 20 has a further cut away portion to expose the mouthpiece 36.

Figure 3:
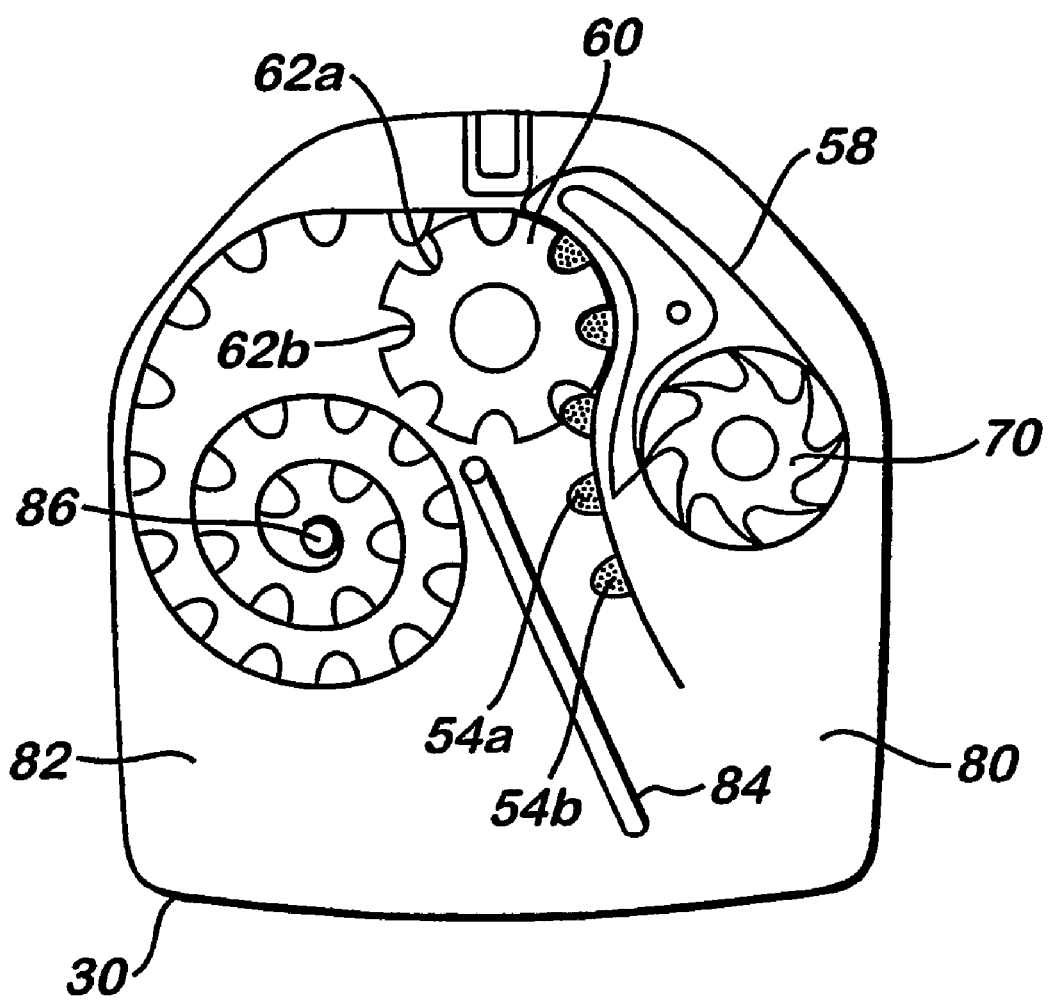
FIG. 3 shows a schematic view of an internal mechanism of a cassette in accordance with an embodiment of the present invention.

FIG. 3 schematically shows an internal mechanism of a refill cassette 30 containing a medicament carrier, in the situation where the majority of the pockets are still filled with discrete doses of medicament in the form of dry powder. The internal mechanism comprises an index wheel 60 and a lid-winding wheel 70 for winding the used portion of the lid sheet 58. The index wheel 60 has a plurality of recesses 62a, 62b extending parallel with the axis of the wheel. The recesses 62a, 62b are spaced at a pitch which is equal to the distance between the centre lines of adjacent pockets 54a, 54b.

The cassette 30 also includes an area 80 for the medicament carrier to be coiled up prior to use of the doses contained inside it and an area 82 where the used base of the medicament carrier is collected. Area 82 contains base winding wheel 86 on which the used portion of the base sheet is wound, and a spindle mechanism (not shown) is arranged to unidirectionally rotate the index wheel 60 and the lid-winding wheel 70 in unison with base winding wheel 86.

In operation, the user moves the holder relative to the body to move the cassette into the dispensing position and then presses on the finger tab of the lever to cause it to move. This leads to rotation of the index wheel 60 which results in rotation of both the base winding wheel 86 and the lid winding wheel 70, thus peeling the base sheet and lid sheet apart over a distance sufficient to expose a previously unopened pocket opposite the end of the powder outlet. The patient can then inhale the powdered medicament through the mouthpiece.

FIG. 2b shows the thumbtab 28 of the indexing lever in a reset position, ready for actuation. Actuation of the thumbtab 28 indexes the medicament carrier within the refill cassette 30, thereby exposing a dose of medicament ready for inhalation through the mouthpiece 36. The display 22 shown in FIG. 2b includes a graphical representation of a set of indicia representative of time elapsed and a set of dose count indicia, to be described in further detail below.

Embodiments of the invention are concerned with aspects of alerting systems, and in particular, with aspects that can be usefully employed by medicament reminder systems. In the context of medicament reminder systems, embodiments are concerned with improving a user's compliance with a preferred regimen, that is to say the correlation between the time that a user actually dispenses medicament and the time that the medicament should be dispensed.

In embodiments of the invention, an alert state is generated based on the time that has elapsed since a previous event, so that the alert state provides the user with information that enables them to ascertain the stage, in relation to the time of the next event, to which the current time corresponds. In the context of medicament dispensers, an event comprises taking a dose of medicament, so that the alert state provides the user with information that enables them to ascertain the stage, in relation to the time of the next scheduled dose, to which the current time corresponds. In one embodiment, the stages include "early" or "due" or "late". The alert states are presented proactively, prior to the activation of a next event relating to the dispensing of medicament. Thus an alert state can be presented at a time that corresponds to an "early", "due" or "late" stage of elapsed time.

Various embodiments of the invention, integrated with a medicament dispenser, will now be described in more detail.

Figure 4:
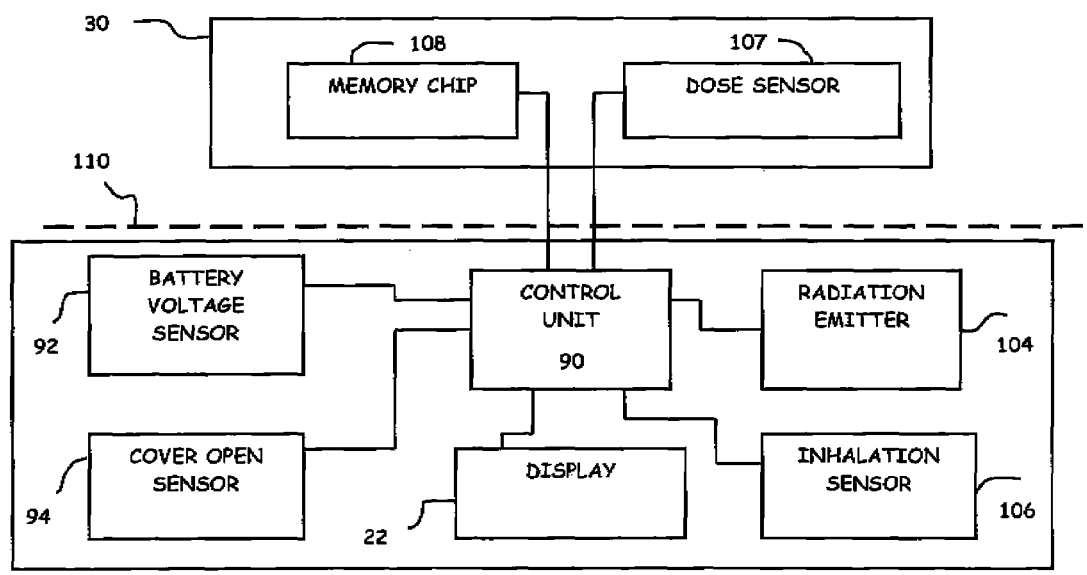
FIG. 4 is a schematic block diagram of an electronic subsystem of the medicament dispenser.

FIG. 4 is a schematic block diagram of the electronic subsystem of the medicament dispenser. The holder 20 includes an in-built control unit 90, for example in the form of a microprocessor chip, including an internal clock. Various sensors are electrically connected to the control unit 90, including a battery voltage sensor 92, which monitors, against a threshold, voltage of a battery providing electrical power to the medicament dispenser, also housed in the holder 20. In some arrangements, the control unit 90 can include a cover open sensor 94, which senses movement of the cover relative to the holder from the non-dispensing position, in which the cover covers the mouthpiece of the dispenser, to an open position in which medicament may be dispensed.

The control unit 90 also includes means for detecting that a dose has been taken; in a first arrangement the means comprises dose sensor 107, which is part of the refill cassette 30. The dose sensor 107 is in data communication with the control unit 90 via a data communication interface 110, which uses a transceiver in the control unit 90 and a transceiver in the sensor 107. When the index wheel 60 is rotated, the dose sensor 107 senses said rotation, and transmits a signal to the control unit 90 indicating that a dose is about to be taken (the assumption being that a dose will subsequently be taken). In a second arrangement the means for detecting that a dose has been taken is provided by a radiation emitter 104, which emits radiation into the mouthpiece, and inhalation sensor 106, which detects the emitted radiation on the other side of the mouthpiece. When the user inhales, the medicament powder causing scattering of the radiation emitted by radiation emitter 104, thereby reducing the detected level of radiation at inhalation sensor 106, indicating the inhalation of a dose. The control unit 90 and base unit comprise fewer components in the first arrangement, and is the preferred arrangement. The control unit 90 is operatively connected to the display 22, for controlling the display in accordance with an alert state.

Various different conditions of the medicament dispenser may be sensed by means of the electronic subsystem illustrated in FIG. 4. These include the stage of elapsed time since a previous dose was dispensed; after a dose is dispensed and/or inhaled, the control unit 90 begins a time elapsed function, which monitors time that has elapsed since a dose was sensed to have been taken. This elapsed time is used by the control unit 90 to select an alert state, which is displayed on the display 22. Thus in this embodiment the alerting system is provided by the control unit 90.

Each of FIGS. 5–16 shows alternative embodiments of screen configuration for the display 22, whereby the alert states may be indicated to the user. In at least one embodiment each of the alert states is embodied as a display mode and presented on a segmented LCD display. Note that, below, the description of elements of each of the screen configurations is to be understood to apply to the same indicia displayed in each of the different screen configurations where the same numerical references, incremented by multiples of 100, are used. Although the exact form of the indicia are different, their functions and the control thereof by the control unit 90 are similar and therefore should be understood that the description in relation to indicia in one configuration applies equally to similarly referenced indicia in different configurations.

Figure 5:
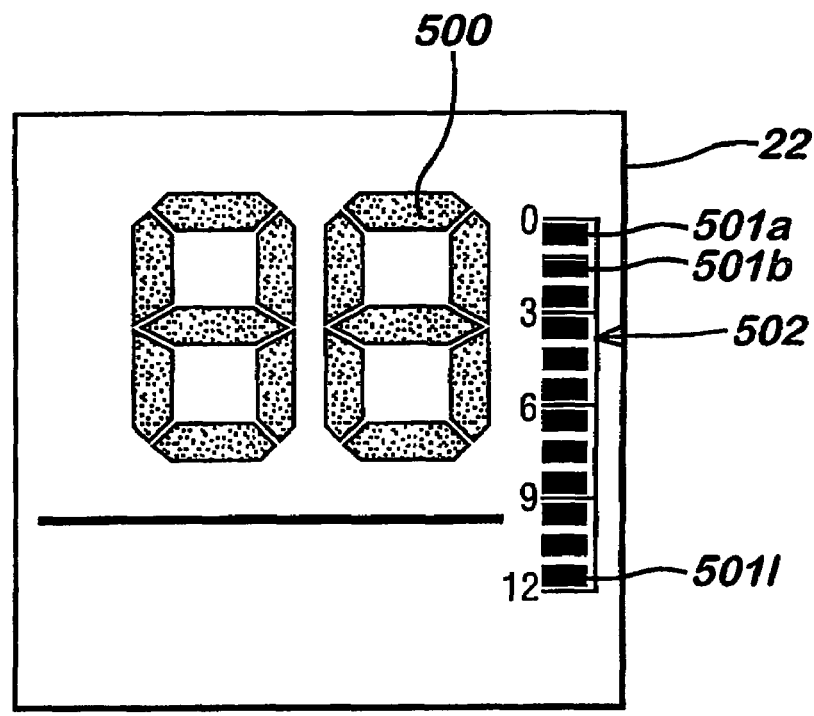

Referring firstly to FIG. 5, in a first embodiment the display configuration 22 comprises dose count indicia 500 and a display mode 502 having one or more separately activatable regions 501a . . . 501l, which for example each separately indicates a further period that has elapsed since the time of last taking a dose. Each display mode thus corresponds to a particular arrangement of regions and, since the display mode changes in accordance with increasing elapsed time, the display mode indicates the stage of elapsed time. In this configuration, each region corresponds to a period of 1 hour.

Figure 6:
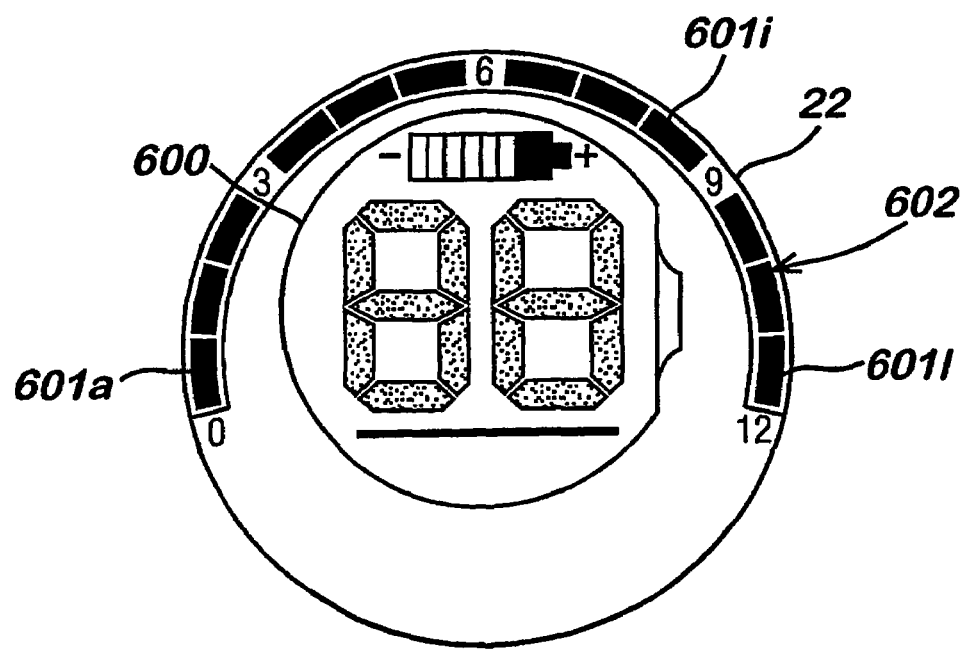
Figure 7:
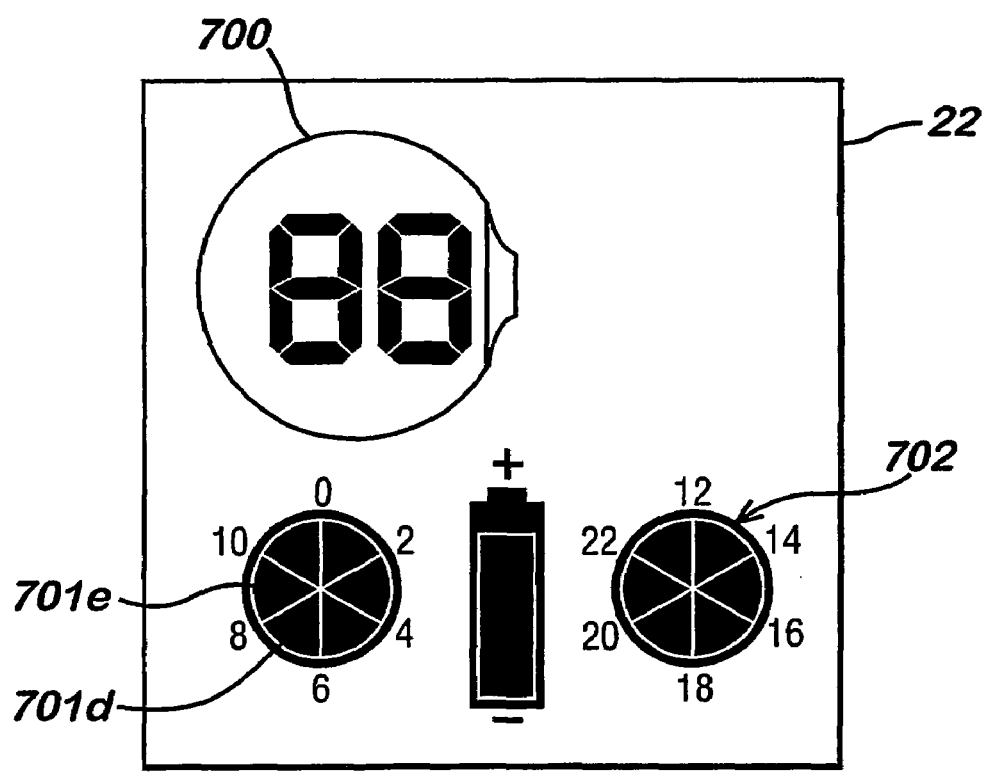

FIG. 6 shows an alternative arrangement, where the activatable regions 601a . . . 601l are positioned around the periphery of the display 22, and FIG. 7 shows a yet further alternative arrangement, where each activatable region 701a . . . 701l corresponds to 2 hours and forms a segment of a circle.

Figure 8D:
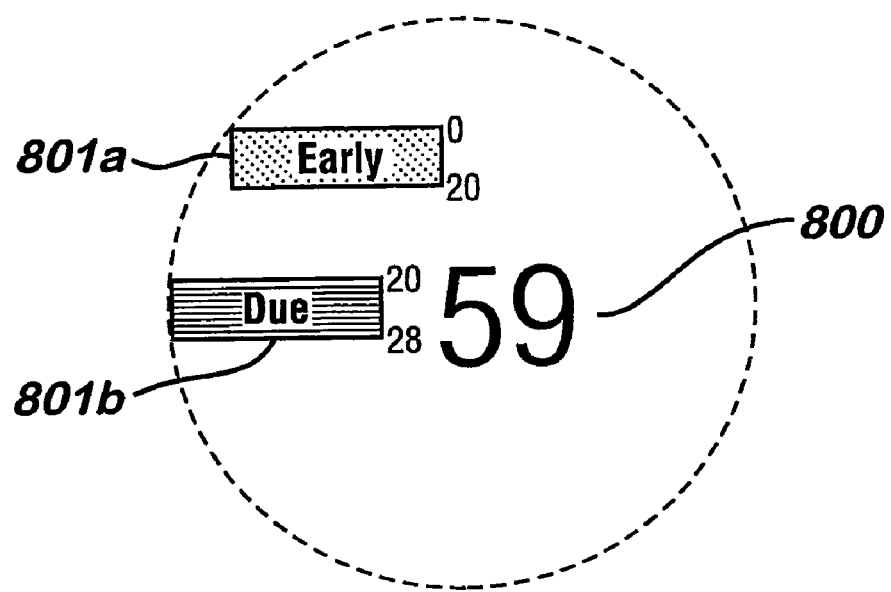
Figure 8E:
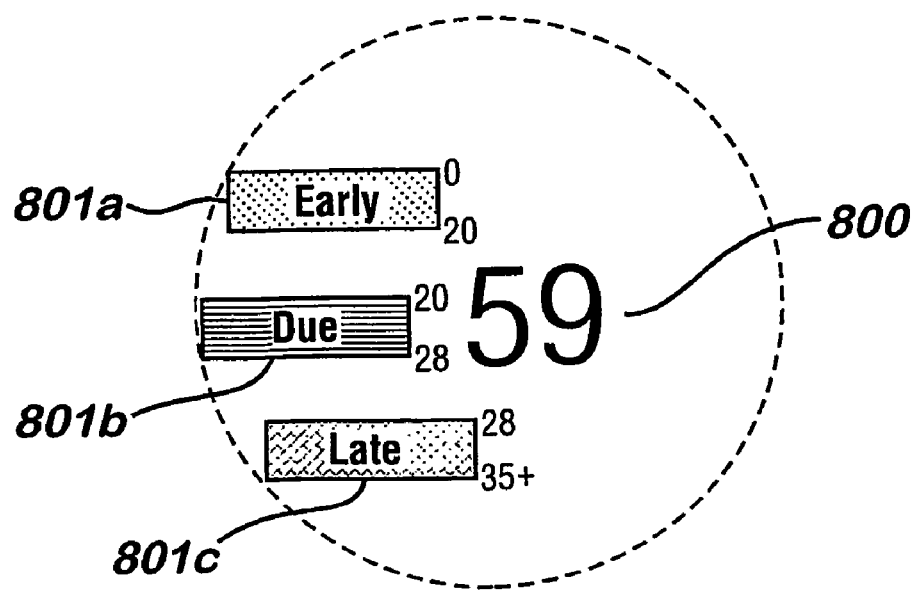
Figure 9A:
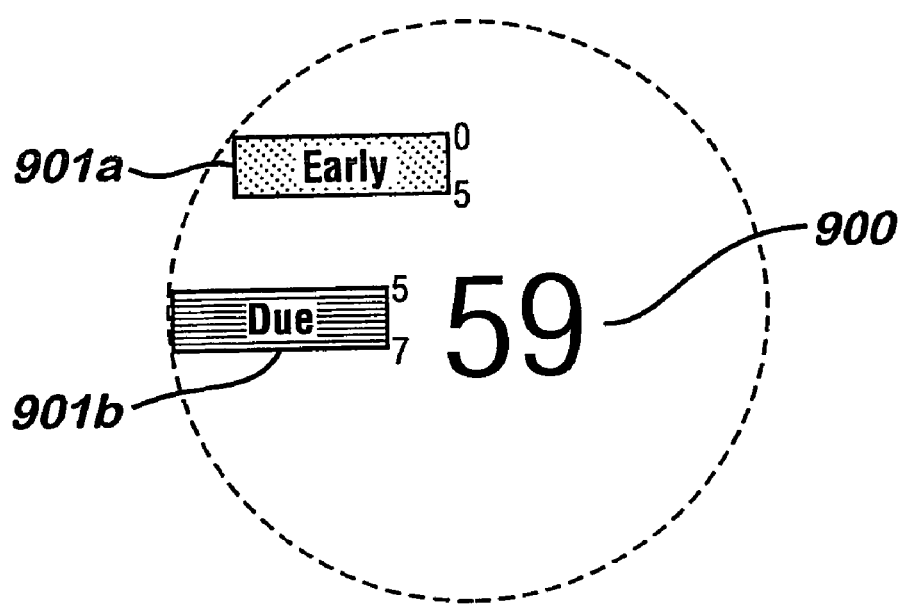
Figure 9B:
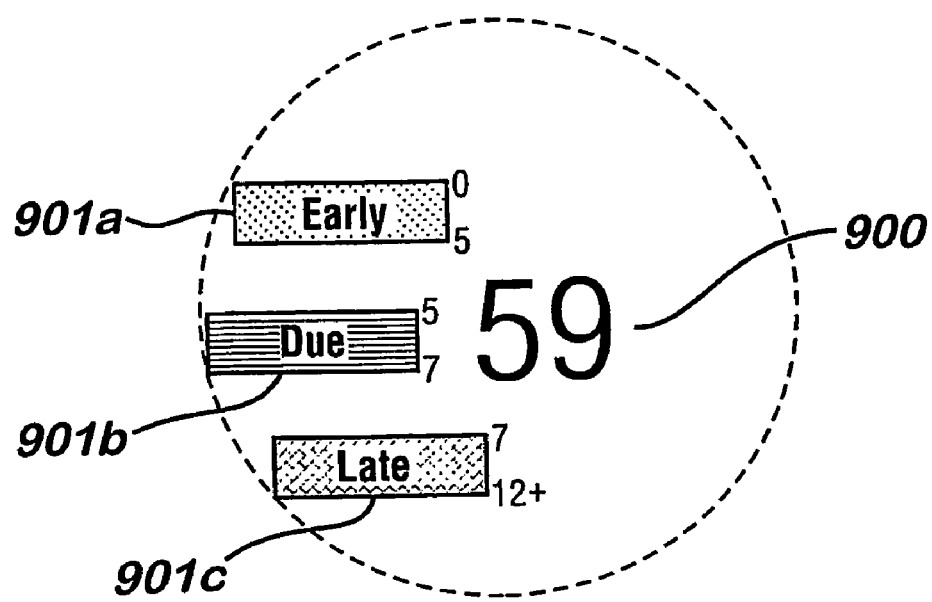

Referring now to FIGS. 8a–8e, a second embodiment will be described for the case where a dose should be taken every 24 hours (herein referred to as a "once a day regimen"). In this embodiment there are three display modes, a first displaying early activatable region 801a (FIG. 8a), a second displaying due activatable region 801b (FIG. 8b) and a third displaying late activatable region 801c (FIG. 8c). In the figures, these regions 801a, 801b, 801c are assigned different patterns (dots, stripes, bricks respectively) to aid identification of a particular region, and the words "early", "due" and "late", which explicitly define the different stages, are shown on the Figures for clarity only (that is to say that the screen 22 would preferably not display the text). Preferably each region 801a, 801b, 801c would have a different colour, and the user would be informed which colour relates to the different stages. As an alternative to a display mode displaying a single region corresponding to the current stage of elapsed time, each display mode could display regions indicative of current and previous stages. Thus, referring to FIGS. 8d and 8e, both the "early" region 801a and the "due" region 801b are shown when the elapsed time falls within the "due" region, and, when the elapsed time falls within the "late" region, all three regions 801a, 801b, 801c are shown. The arrangement shown in FIGS. 8d, 8e has the advantage of allowing the user to track his progress through the various stages, and means that he does not have to remember which region refers to which stage: if there are three regions in total and only two are displayed, the currently elapsed time must correspond to the "due" stage.

A particular feature of this embodiment is that the regions correspond to periods of different lengths, and it may be expected that the lengths will be dependent on the sensitivity to deviation from a strict 24 hour interval (and thus be medicament dependent); if, for example, a dose should not be taken more frequently than every 20 hours, the "early" region will extend from t=0 to at least t=20; similarly, if a gap of no more than 28 hours is allowable between consecutive doses, the "late" region will extend from t=28 onwards (the "late" region displaying, say, t=35+, where the "+" indicates that the currently elapsed time could be in excess of 35 hours).

The embodiment shown in FIGS. 8a–8e can be modified so as to be suitable for each of the twice, thrice and four times a day regimens: where a regimen involves an increasing number of doses, the regions correspond to shorter time periods. Thus, referring to FIGS. 9a and 9b, for the four times a day regimen, the early region 901a could extend between t=0 and t=5 hours, while the due region 901b could correspond to t=5 to t=7 hours and the late region 901c could correspond to t=7 to t=12+ hours.

Advantageously medicament dispensers can be manufactured as commercial off the shelf dispensers, each corresponding to a specific regimen, and not requiring programming in accordance with specific regimens. This means that cheaper dispensers can be made and a physician can simply prescribe whichever dispenser is appropriate for the user's medication and regimen, thereby removing the need to perform any additional steps in dependence on type of medicament (such as reading information from the medicament and programming the dispenser to present an alert state).

Figure 10A:
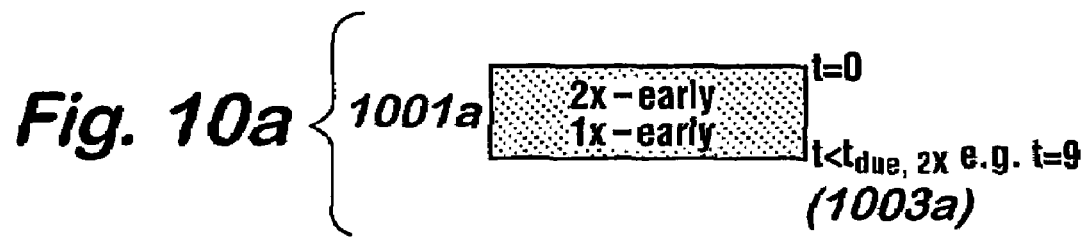
Figure 10B:
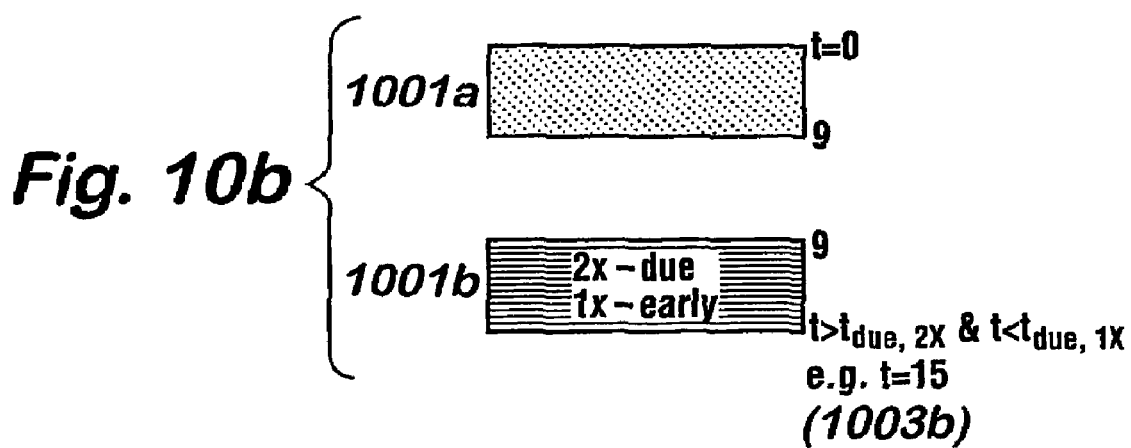

FIGS. 10a, 10b, 10c and 10d show display modes corresponding to a third embodiment, which can be used for both the once and twice a day regimens. In these figures the display mode is shown without the backdrop of the screen 22; (from the earlier figures the skilled person would appreciate that the display modes could, for example, be presented on the left hand side of the screen 22, or around the periphery of the screen 22). Referring firstly to FIG. 10a, a first display mode containing region 1001a indicates an early stage for both regimens; referring to FIG. 10b, a second display mode including region 1001b indicates a "dose due" stage for the twice a day regimen and an "early" stage for the once a day regimen. In the event that a user is on the twice a day regimen, and they take a dose during the time corresponding to this second display mode, the dispenser will automatically revert to the first display mode (showing region 1001a). Thus in the event that a twice daily user always takes the dose during the "dose due" stage, the dispenser will not operate in any more than the first two display modes.

Referring to FIG. 10c, and assuming that the user has not taken a dose, then when the elapsed time exceeds 15 hours, a third display mode including region 1001c will be activated, indicating a "late" stage for the twice a day regimen and a "dose due" stage for the once a day regimen. Assuming that the user does not take a dose while the third display mode is activated, the dispenser will ultimately display a display mode containing region 1001d, indicating a late stage for both regimens (FIG. 10d). As for the second embodiment, a display mode can simply comprise whichever region 1001a–1001d corresponds to the current stage of elapsed time.

In this third embodiment, the duration corresponding to a respective region 1001a, 1001b, 1001c, 1001d is dependent on features of both regimens: the upper limit $t_{1003a}$ of region 1001a is set to $t_{1003a} < t_{dose\ due\ for\ 2\times\ regimen}$, and may, for example be set to 9 hours; the upper limit $t_{1003b}$ of region 1001b is then set to a time that falls later than the time at which a dose is due for the twice a day regimen and earlier than the time at which a dose is due for the once a day regimen, i.e. $t_{dose\ due\ for\ 2\times\ regimen} < t_{1003b} < t_{dose\ due\ for\ 1\times\ regimen}$ and may, for example, be set to 15 hours; and the upper limit $t_{1003c}$ of region 1001c is set to a time that falls later than the time at which a dose is due for the once a day regimen, i.e. $t_{1003c} > t_{dose\ due\ for\ 1\times\ regimen}$ and may, for example, be set to 30 hours. These times $t_{1003a}$, $t_{1003b}$, $t_{1003c}$ will be dependent on the sensitivity to a deviation from the time at which the next dose is due, as described above. The upper limit $t_{1003d}$ of region 1001d can be set to an arbitrary number of hours in excess of 28 hours, e.g. 40+ hours.

In the event that each region is assigned a different colour (e.g. region 1001a is orange; region 1001b is blue; region 1001c is red and region 1001d is green), the physician can instruct the user as to which colour indicates that his dose is due (e.g. if on a twice daily regimen, the due region could be blue, and if on a once a day regimen, the due region could be red), and which colour region(s) indicates an early or a late stage of elapsed time. The physician may, for example, place a coloured sticker on the cover 10 corresponding to the colour of the appropriate "due" region.

This third embodiment is particularly advantageous from a manufacturing point of view, since the same dispenser can be used for two different regimens and, as for the embodiment described with reference to FIGS. 8a–8e, no additional programming is required, so the dispenser can be relatively simple and cheap. This embodiment can also be applied to both the thrice and four times a day regimens (but the time periods corresponding to the regions, defined by $t_{1003a}$, $t_{1003b}$, $t_{1003c}$ and $t_{1003d}$ will be determined by the constraints of the thrice and four times a day regimens).

In a further arrangement, one, some, or all extents 1003a, 1003b, 1003c, 1003d of the regions can be set manually, by a user, via a configurable timing device (not shown) that is connected to the control unit 90. This means that the same dispenser could be used for all regimes.

Figure 11A:
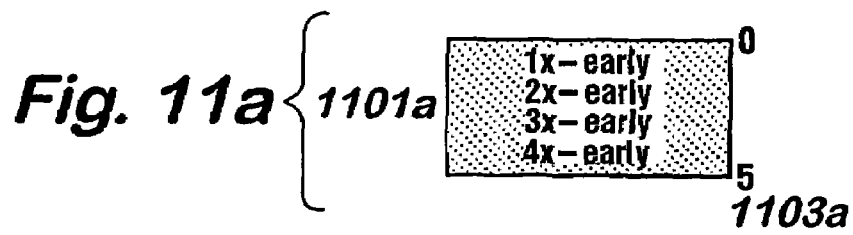

FIGS. 11a, 11b, 11c and 11d, 11e show display modes according to a fourth embodiment, which can be used for the once, twice, thrice and four times a day regimens. As for the third embodiment, these figures are enlarged and presented without the backdrop of the screen 22 for clarity. Referring to FIG. 11a, a first display mode involves displaying region 1101a for an elapsed time of between 0 and 5 hours; this corresponds to an "early" stage of elapsed time in respect of all of the regimens. A second display mode involves displaying region 1101b for an elapsed time of between 5 and 10 hours; this corresponds to an "early" stage of elapsed time in respect of the once and twice daily regimes and a "dose due" stage of elapsed time in respect of the thrice and four times a day regimens (since for the thrice a day regimen a dose is due at 8 hours, and for the four times a day regimen a dose is due at 6 hours). In the event that a user is on either of these regimens, and he takes a dose during a time corresponding to this second display mode, the dispenser will automatically revert to the first display mode 1101a. Thus in the event that a thrice daily or four times a day user always takes the dose during the "dose due" stage, the dispenser will not operate in any more than the first two display modes.

Figure 11B:
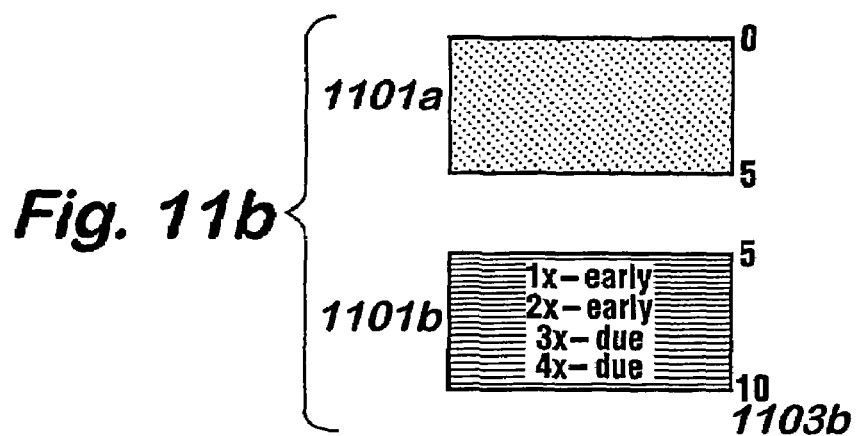
Figure 11C:
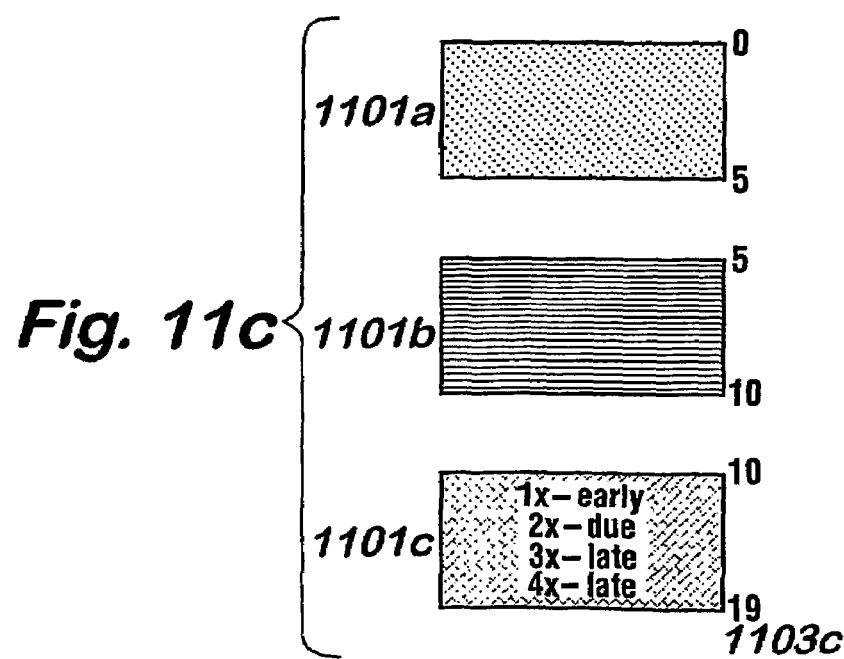

Turning now to FIG. 11c, a third display mode involves displaying region 1101c for an elapsed time of between 10 and 19 hours; this corresponds to a "dose due" stage of elapsed time in respect of the twice daily regime, an "early" stage of elapsed time in respect of the once daily regimen and a "late" stage of elapsed time in respect of the thrice daily and four times a day regimens. In the event that a user is on the twice a day regimen, and he takes a dose during a time corresponding to this third display mode, the dispenser will automatically revert to the first display mode 1101*a*. Thus in the event that a twice daily user always takes the dose during the "dose due" stage, the dispenser will not operate in any more than the first three display modes.

Figure 11D:
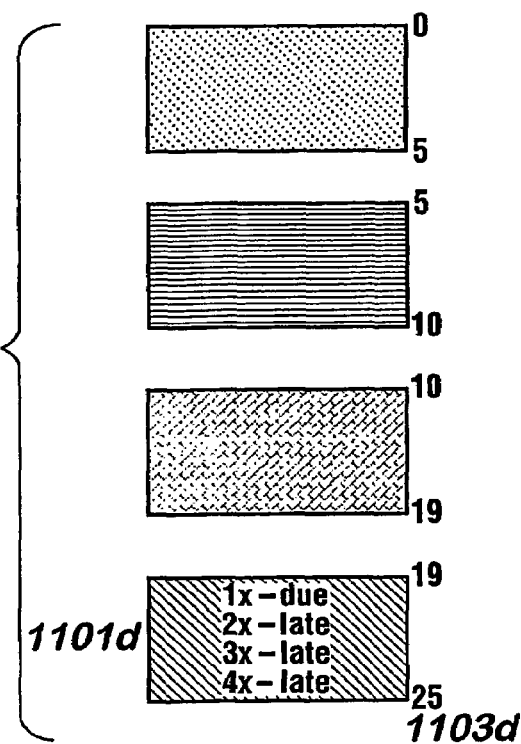
Figure 11E:
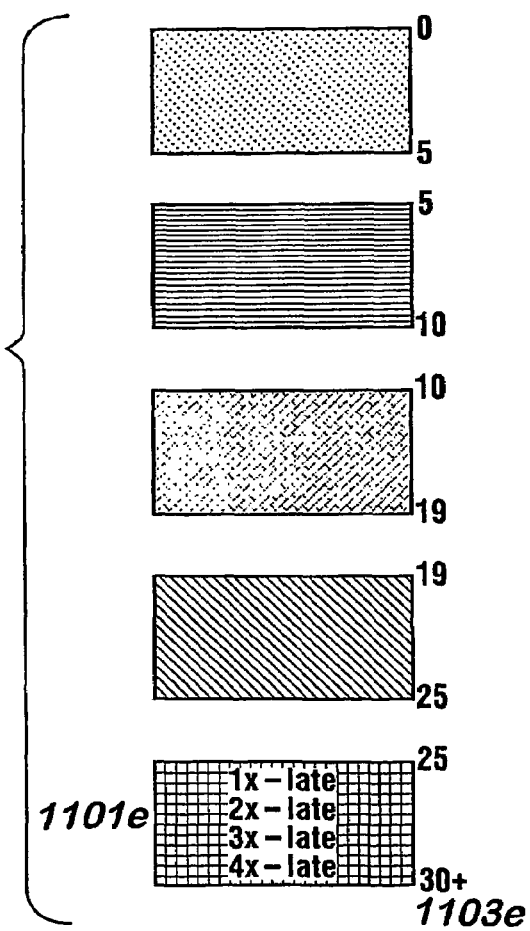

Turning now to FIG. 11*d*, a fourth display mode involves displaying region 1101*d* for an elapsed time of between 19 and 25 hours; this corresponds to a "dose due" stage of elapsed time in respect of the once daily regimen and a "late" stage of elapsed time in respect of the twice, thrice daily and four times a day regimens. In the event that a user is on the once a day regimen, and he takes a dose during a time corresponding to this fourth display mode, the dispenser will automatically revert to the first display mode 1101*a*. Thus in the event that a once a day user always takes the dose during the "dose due" stage, the dispenser will not operate in any more than the first four display modes. Turning finally to FIG. 11*e*, a fifth display mode involves displaying region 1101*e* for an elapsed time in excess of 25 hours. This corresponds to a "late" stage of elapsed time in respect of all of the regimens.

The period of time corresponding to region 1101*c* in the third display mode—the "dose due" stage for the twice a day regimen—is relatively long; if the twice a day regimen user were to take a dose towards the end of this period, this may lead to unsafe deviations from the twice a day regimen. Thus, in an alternative arrangement, the fourth embodiment could involve shortening the period corresponding to region 1101*c* to between 10 and 15 hours and displaying a further display mode for an elapsed time of between 15 and 20 hours; this further mode, which is activated at 15 hours instead of 19 hours, would correspond to an "early" stage of elapsed time in respect of the once daily regimen, and a "late" stage of elapsed time in respect of the twice, thrice daily and four times a day regimens. Thus, none of the regions in this display mode correspond to "dose due", meaning that this further display mode would not serve the purpose of prompting the user to take a dose. However, it would serve the purpose of reducing the deviation from the ideal spacing between successive doses on a twice a day regimen, since the user would know that he is in a "late" stage of elapsed time sooner than is possible with the arrangement shown in FIG. 11*c*.

This fourth embodiment is especially advantageous from a manufacturing point of view, since the same dispenser can be used for four different regimens and, as for the embodiment described with reference to FIGS. 8*a*–8*e*, no additional programming is required, so the dispenser can be relatively simple, and thus cheap. This embodiment is also relatively straightforward from a user point of view: when prescribing the dispenser, the physician would merely have to instruct the user regarding the display mode that is relevant to the user's regime. In the event that the regions are of different colours (e.g. region 1101*a* orange; region 1101*b* blue; region 1101*c* red; region 1101*d* green; region 1101*e* yellow; and region 1101*f* mauve), the physician would identify whichever colour corresponds to the "dose due" stage for the user's regimen and instruct the user to take a dose when the display 22 shows that colour (optionally placing a sticker of the appropriate colour on the cover 10, as described above). The physician could additionally indicate the colour of the "early" stage of elapsed time, and when more than one region corresponds to "early" stage (as is the case for, e.g. the once a day regimen), the physician could simply indicate the colour of the region immediately preceding the "dose due" region. This would enable the user to prepare for the fact that a dose will fall due shortly. Conversely, the physician could indicate the colour of the region that corresponds to one or more "late" stages.

Figure 12A:
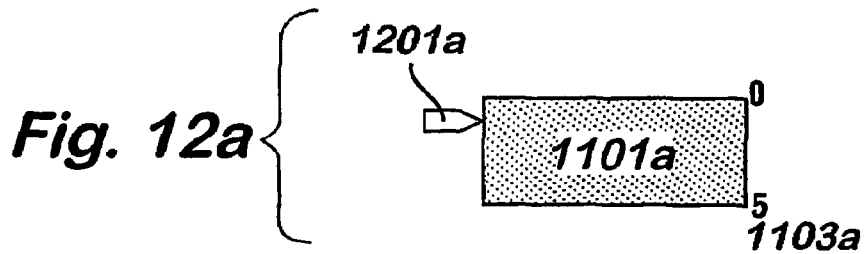
Figure 12B:
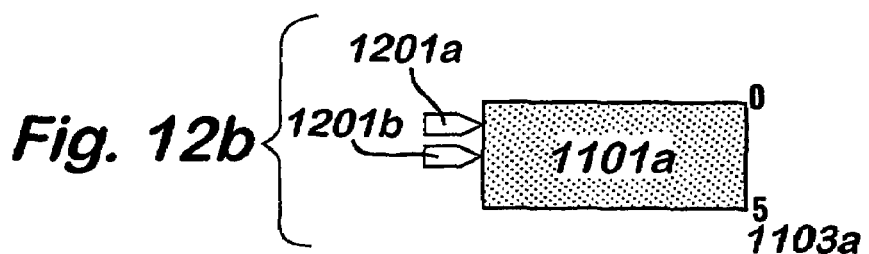
Figure 12C:
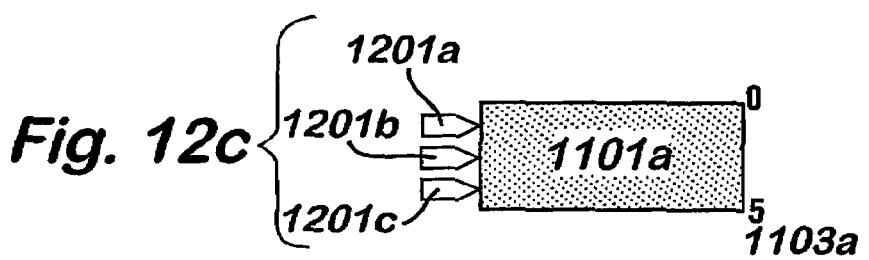
Figure 12D:
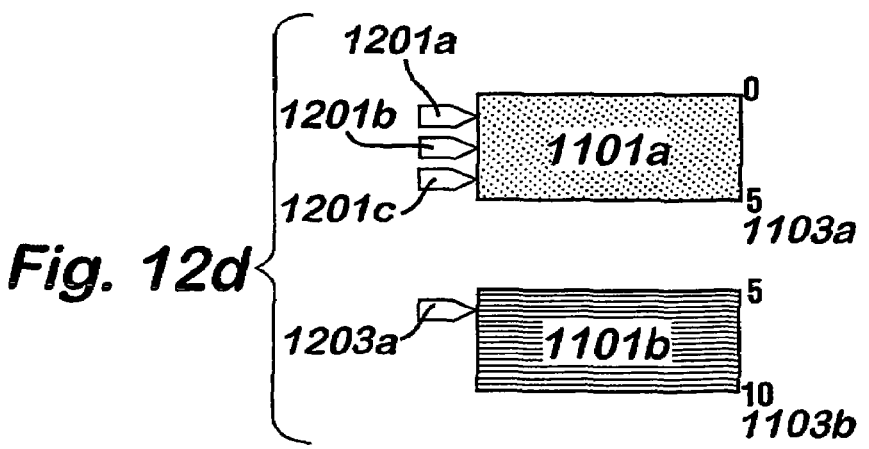

A fifth embodiment of the invention is shown in FIGS. 12*a*–12*f*, which correspond to FIGS. 11*a* and 11*b* of the fourth embodiment, with the addition of gradations indicative of the proportion of time, within a region, that has elapsed. Thus referring to FIGS. 12*a*–12*c*, during the first display mode, while region 1101*a* is displayed, between 0 and 1.67 hours, a first gradation mark 1201*a* is also displayed; between 1.67 hours and 3.23 hours, a second gradation mark 1201*b* is displayed; and between 3.23 hours and 5 hours a third gradation mark 1201*c* is displayed. Referring to FIGS. 12*d* and 12*e*, during the second display mode, while region 1101*b* is displayed, between 5 and 6.67 hours a fourth gradation mark 1203*a* is displayed; between 6.67 hours and 8.23 hours a fifth gradation mark 1203*b* is displayed; and between 8.23 hours and 10 hours a sixth gradation mark 1203*c* is displayed. It will be appreciated that the number of gradations is a design choice that is dependent on, for example, the constraints of the display 22 and medical constraints.

An advantage of this embodiment is that a user can see amount of time that has elapsed to a greater degree of accuracy than is possible with the previous embodiments, which can be useful in minimising irregularity in inter-dose intervals. This embodiment is particularly useful in the context of the fourth embodiment, where the second display mode corresponds to the "dose due" stage for both the third and fourth regimens, since it enables the user to differentiate the time that a dose is due for the thrice a day regimen (fifth gradation 1203*b*) from the time that a dose is due for the four times a day regimen (fourth gradation 1203*a*).

Figure 13A:
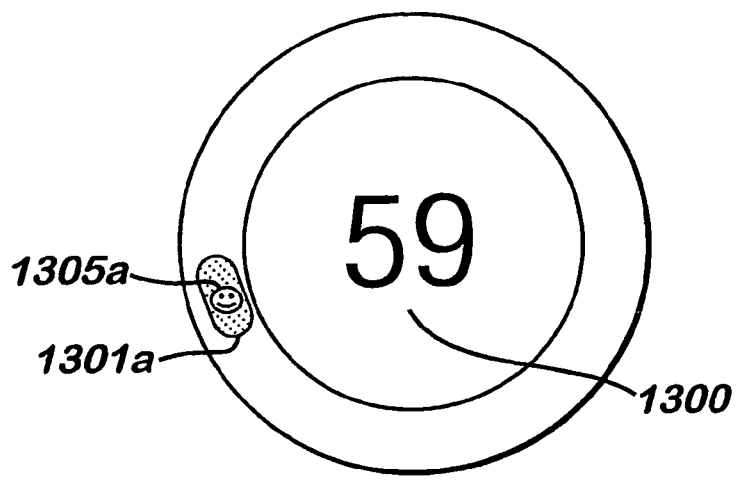
Figure 13B:
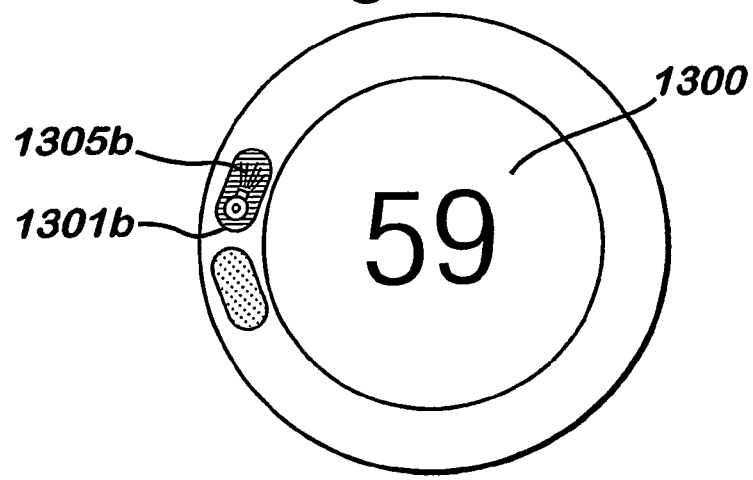
Figure 13C:
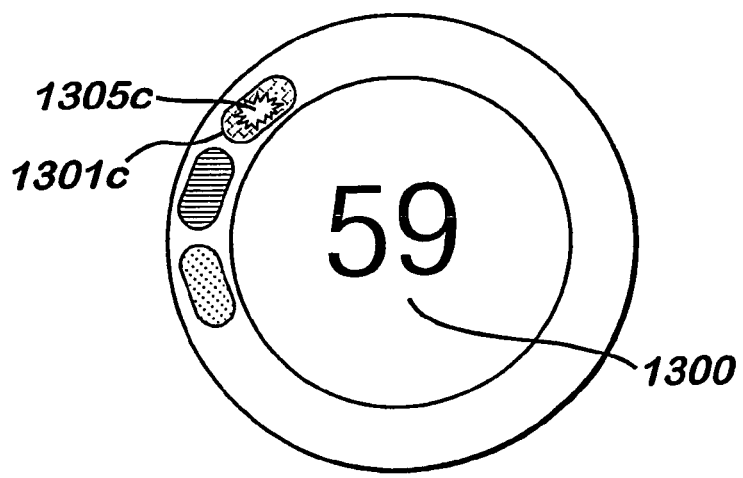

A sixth embodiment is now described, with reference to FIGS. 13*a*–13*c*, for an alternative arrangement wherein the display modes are presented around the periphery of the display 22. In this sixth embodiment, regimen information associated with the refill cassette 30 is utilised. Referring back to FIG. 4, the refill cassette 30 includes a memory chip 108, which is in data communication with the control unit 90 via a data communication interface 110. The control unit 90 uses a timing regimen, which may be preset in the control unit 90 or read from the memory chip 108, to determine the length of time between dose reminders. If the current elapsed time since the taking the last dose is less than or greater than the dose reminder interval, a dose not due or a dose due condition is generated by the control unit 90, causing respectively "dose not due" indicia 1305*a* or "dose due" 1305*b* to be displayed on whichever region corresponds to the currently elapsed time.

This embodiment will now be exemplified using the once a day regimen shown in FIGS. 8*a*, 8*b* and 8*c*, assuming that the dose reminder interval read from the chip 108 is 24 hours. During the "early" stage of elapsed time, the first display mode is activated (displaying region 1301*a*) and the "dose not due" indicia 1305*a* is displayed. When the currently elapsed time reaches 20 hours, the second display mode, thus region 1301*b*, is activated (shown in FIG. 13*b*). When the currently elapsed time reaches 24 hours, the display mode is modified to include "dose due" indicia 1305*b*; preferably, the dose due indicia 1305*b* is alternately switched on and off to highlight to the user that their dose is due. In the event that the currently elapsed time exceeds the dose reminder interval, and the control unit 90 detects that no dose has yet been taken, the control unit 90 proceeds as per the second embodiment, activating the third display mode when the elapsed time reaches 28 hours. In this situation, the third display mode can include the "dose due" indicia, as shown in FIG. 13c, or alternatively "late dose" indicia 1305c, which may flash intermittently.

FIGS. 14a–14e show a seventh embodiment of the invention, which involves use of a bezel 40. The bezel 40 is removably connected to the holder 20 via lugs 41a, 41b, 41c (41c not shown), which engage in a groove (not shown) in holder 20, the groove being located above the display 22. The bezel 40 has a transparent annular portion 41 located between limiters A1, A2, while the remainder of the annulus (portion 42) is obscured. As can be seen from FIG. 14b, the transparent portion 41 is dimensioned such that, when connected to the holder 20 via the clips 41a, 41b, 41c, parts of the display underneath the annular portion 41 can be seen while parts under the obscured portion 42 cannot. Conveniently the bezel 40 can assume a plurality of positions, or orientations with respect to the display, since the groove in the holder 20 can extend around the whole outer perimeter of the display 22, enabling lugs 41a, 41b, 41c to engage at any position in the groove. Alternatively the holder 20 can have a plurality of grooves of a specified length, each groove corresponding to one of the lugs 41a, 41b, 41c.

Figure 14A:
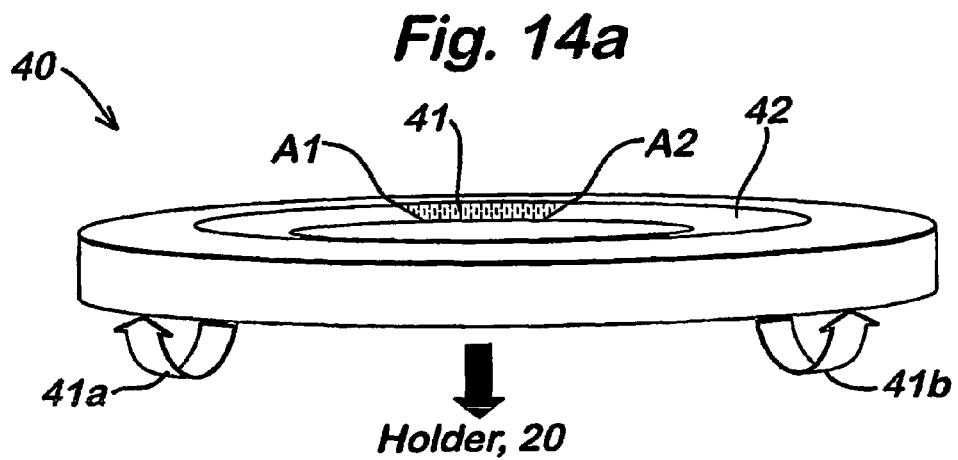
FIGS. 14a and 14b are schematic diagrams showing a bezel according to a seventh embodiment of the invention, configured to engage with the holder of FIG. 1.
Figure 14B:
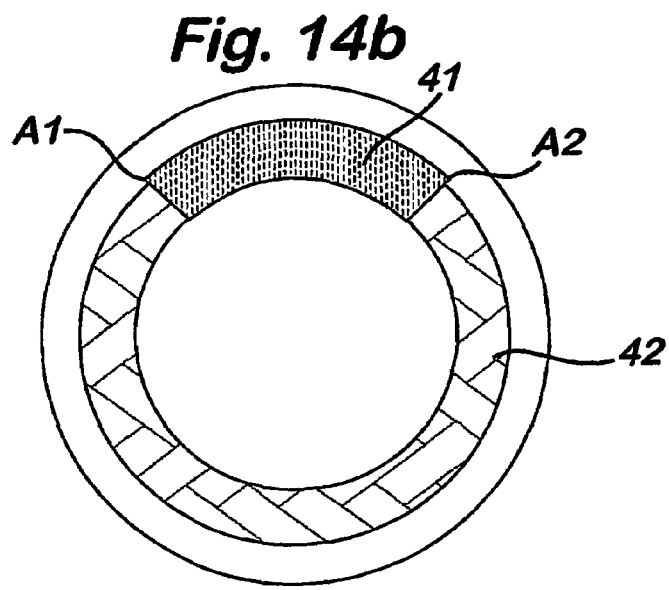
Figure 14C:
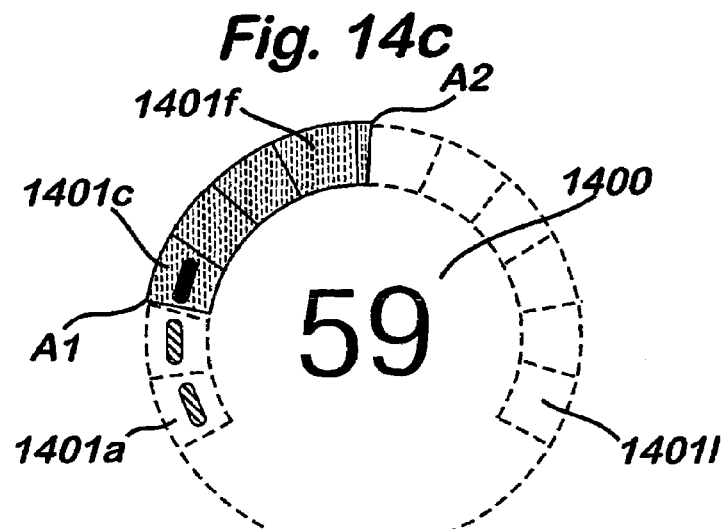
Figure 14D:
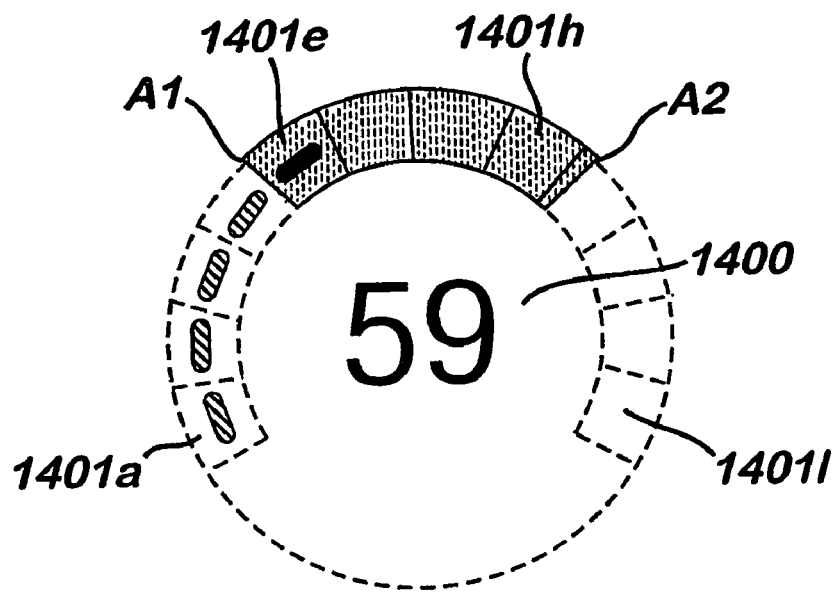
Figure 14E:
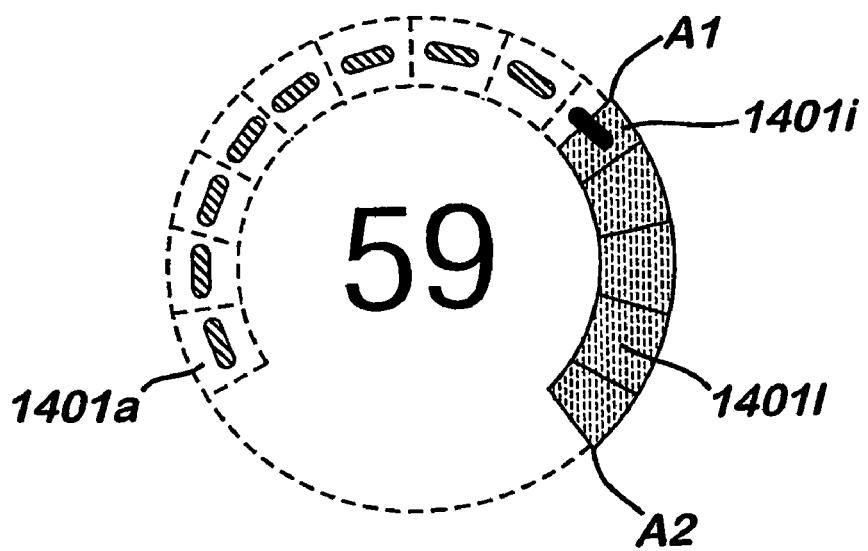

FIGS. 14c, 14d, 14e show the bezel in three different positions, respectively corresponding to a thrice, twice and once a day regimen, superimposed upon display 22. As for the first embodiment, the display indicia includes a plurality of separately activatable regions 1401a . . . 1401l, which each separately indicates a further period that has elapsed since the time of last taking a dose. In this configuration, each region corresponds to a period of 2 hours, and each region 1401a . . . 1401l is activated upon passage of a further 2 hours. Referring firstly to FIG. 14c, for the thrice a day regimen, the bezel 40 is positioned such that the annular portion 41 is laid over regions 1401c through 1401f, meaning that all portions except 1401c through 1401f are obscured from view (the cross-hatch of regions 1401a, 1401b indicates that, despite being activated, these regions cannot be seen with the bezel 40 in place). In the event that the user takes the dose while regions 1401c . . . 1401f are activated, the control unit 90 will automatically reset the clock, thereby activating region 1401a (which will of course be unseen). Referring next to FIG. 14d, for the twice a day regimen, the bezel is positioned such that the annular portion 41 is laid over regions 1401e through 1401h, meaning that all portions except 1401e through 1401h are obscured from view; in the event that the user takes the dose while regions 1401e . . . 1401h are activated, the control unit 90 will automatically reset the clock, thereby activating region 1401a. Referring next to FIG. 14e, for the once a day regimen, the bezel is positioned such that the annular portion 41 is laid over regions 1401i through 1401l, meaning that all portions except 1401i through 1401l are obscured from view; in the event that the user takes the dose while regions 1401i . . . 1401l are activated, the control unit 90 will automatically reset the clock, thereby activating region 1401a.

An advantage of this embodiment is that the same medicament dispenser and bezel can be used irrespective of regimen; the bezel 40 simply has to be positioned in an appropriate position with respect to the display 22 (e.g. by a physician), and the user instructed to take a dose when he/she sees a region being activated.

Figure 15A:
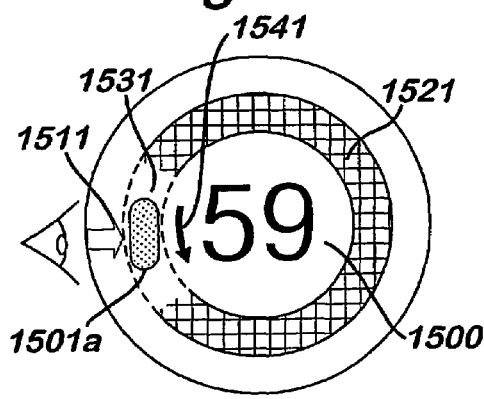
Figure 15B:
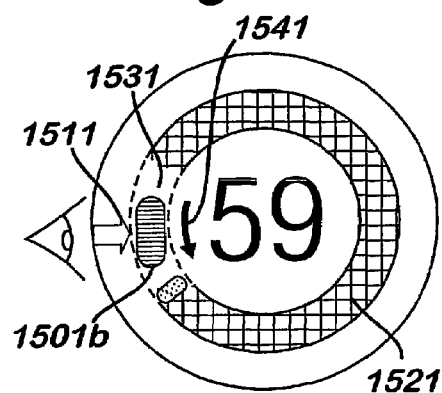
Figure 15C:
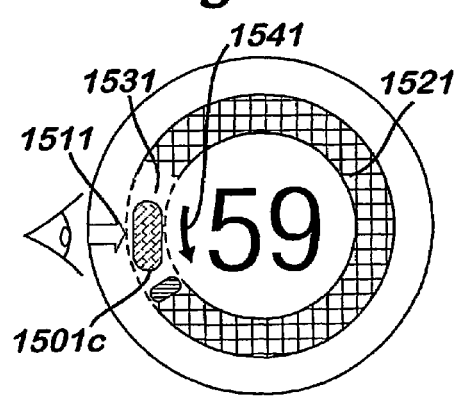
Figure 15D:
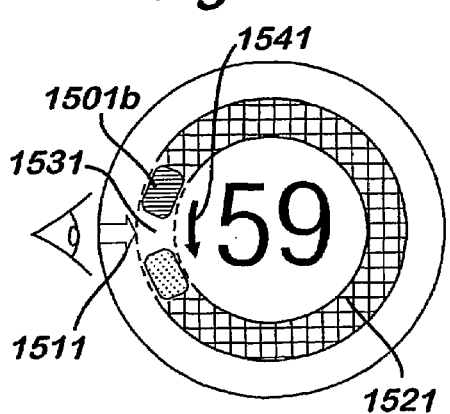

An eighth embodiment is now described with reference to FIGS. 15a–15d. In this embodiment, the screen 22 includes arrow indicia 1511, which is preferably formed from static indicia, and an opaque cover 1521 that is positioned so as to obscure an arcuate annular portion of the display 22, leaving portion 1531 visible. The indicia 1501a, 1501b, 1501c are distributed over the obscured and visible portions, and rotate, as indicated by arrow 1541, around the display 22. Thus their positions, within these sections, change over time, and different indicia 1501a, 1501b, 1501c align with the arrow 1511 at different times. In one arrangement the display mode changes discretely such that the first display mode, involving displaying region 1501a in portion 1531, is activated during the "early" stage of elapsed time; the second display mode, involving displaying region 1501b in portion 1531, is activated during the "dose due" stage of elapsed time; and the third display mode, involving displaying region 1501c in portion 1531, is activated during the "late" stage of elapsed time. Alternatively the display mode can change continuously, meaning that the rotation of the indicia correlates with real time; this means that, at certain times, the arrow 1511 can be expected to align with what appears to be a transition between the display modes (as shown in FIG. 15d). This arrangement is particularly useful to the user since it enables him to see the proportion of time that has elapsed within a stage, and is an alternative to the fifth embodiment.

Figure 16A:
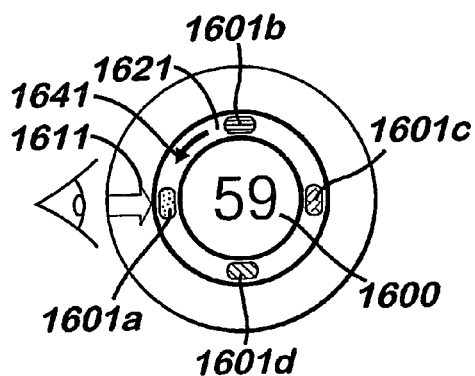
Figure 16B:
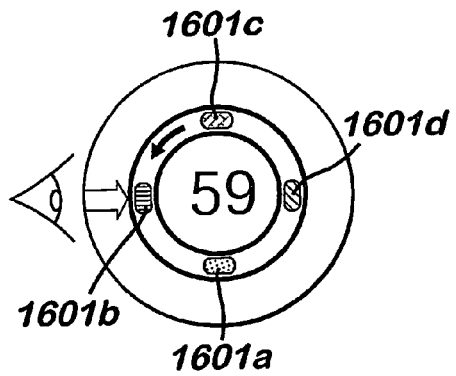
Figure 16C:
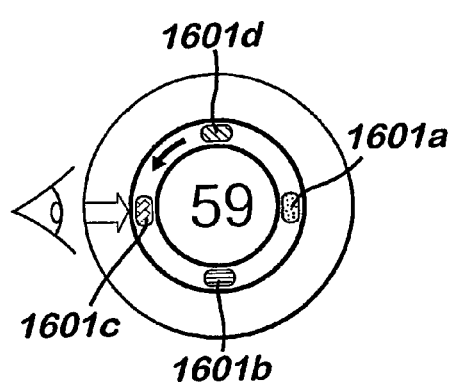
Figure 16D:
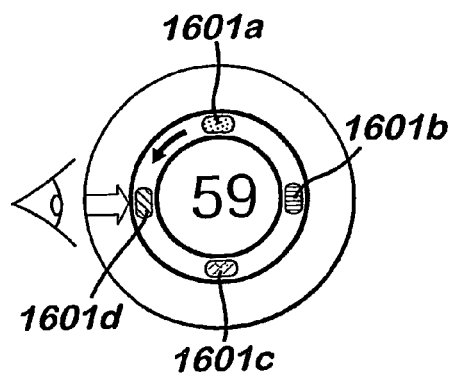

A ninth embodiment will now be described, with reference to FIGS. 16a–16d. In this embodiment the display 22 includes an arrow indicia 1611 and annular display region 1621, and activation of a display mode involves rotation of the annular display region 1621. Preferably the regions 1601a, 1601b, 1601c, 1601d are static indicia, which, as annular region 1621 rotates relative to the screen 22, rotate (indicated by movement arrow 1641) relative to the arrow indicia 1611. Operation of this embodiment will now be described for a medicament dispenser that is configured for both the once a day and twice a day regimens. After a dose has been taken, the first display mode ("early" stage of elapsed time for both regimens) is activated (FIG. 16a), involving alignment of region 1601a with the arrow indicia 1611. As the elapsed time increases, the second display mode, which relates to an "early" stage of elapsed time for the once a day and "dose due" stage of elapsed time for the twice a day regimen, is activated, involving alignment of region 1601b with the arrow indicia 1611 (FIG. 16b). Assuming a dose is not taken, the third display mode, which relates to an "dose due" stage of elapsed time for the once a day and "late" stage of elapsed time for the twice a day regimen, is subsequently activated, resulting in alignment of region 1601c with the arrow indicia 1611 (FIG. 16c). Assuming a dose is not taken, the fourth display mode, which relates to a "late" stage of elapsed time for both regimens, is activated, involving alignment of region 1601d with the arrow 1611 (FIG. 16d). In order to rotate the display region 1621, the holder 20 could include a motor coupled to the control unit 90, which would be arranged to move the display region 1621 in the manner described above.

FIGS. 8a to 16d illustrate use of the display configuration shown in FIG. 5 to present various alert states to a user. In one arrangement the display is not activated unless opening of the cover 10 is sensed (sensor 94), thereby reducing the power consumption of the battery within the base unit. In this arrangement, when the cover 10 is opened, the cover open sensor 94 senses the opening of the cover, and in response control unit 90 displays the current operating conditions of the medicament dispenser on the display 22. After a preset period of inactivity by the user, the display may again be powered down. Alternatively, and if there is sufficient battery power, the display may be permanently activated; this can simplify the electronic subsystem of the dispenser.

Note that although not illustrated in FIGS. 5 to 16d, the electronic subsystem may also include other forms of indicators, such as an audible alarm generator, which may be used, alone or in combination with visual display on the display, to indicate an alert state. For example, when an alert state includes a region corresponding to a "dose due" stage of elapsed time, the medicament dispenser may provide an audible alarm at intervals which increase in frequency and/or volume whilst the dose due condition remains. Alternatively, the control unit 90 may present indicia at different alert rates—e.g. in the form of flashing Light Emitting Diodes (LED) or display elements in the display 22—in dependence on the stage of elapsed time. When an alert state includes a region corresponding to "late" stage of elapsed time, the control unit 90 could be arranged display the late region intermittently, in an attempt to attract the user's attention.

In the above, the display 22 takes the form of a segmented LCD display. In a segmented LCD display, the display indicia are formed by means of individual liquid crystal elements which are preconfigured in the display screen, and which may be separately activated under the control of the control unit 90. An advantage of using a segmented display is increased clarity, along with reduced cost. The display may be monochrome or colour. Again, for increased clarity and reduced cost, a monochrome display is preferred. The display may take other forms, for example, comprise a screen such as an LED arrangement or a pixellated LCD display. The display may be embodied using analogue or digital technology.

Whilst the memory chip 108 is described as communicating with the control unit 90 via electrical contacts, the memory chip 108 may be in the form of a radio frequency (RFID) tag, and the data communications interface 110 may be a wireless data communications interface.

In the above, detectors are used to sense a condition of the medicament detector. However, any actuation detector or release detector that comprises a sensor for detecting any suitable parameter such as movement could be used. Any suitable sensors are envisaged including the use of optical sensors and electrical contact switches. The release detector may sense any parameter affected by release of the medicament such as pressure, temperature, sound, moisture, carbon dioxide concentration and oxygen concentration.

A medicament dispenser according to the invention is suitable for dispensing medicament, particularly for the treatment of respiratory disorders such as asthma and chronic obstructive pulmonary disease (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl)ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2ethyl-2H-tetrazol-5-yl)-tetrahydro-furan-3,4-diol (e.g. as maleate); α$_4$ integrin inhibitors e.g. (2S)-3-[4-({[4-(aminocarbonyl)-1-piperidinyl]carbonyl}oxy) phenyl]-2-[((2S)-4-methyl-2-{[2-(2-methylphenoxy)acetyl] amino}pentanoyl) amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the invention extends to modifications, variations and improvements thereto, and that any elements of the different embodiments may be combined to form further embodiments of the invention.

Note that, in other applications of the invention, the base unit, refill container and/or medicament carrier may take a variety of different forms. Correspondingly, the icons or other graphical representations used may similarly take a variety of different forms. The invention may be used for purposes other than informing a taker of medicament; for example the display functionality may be used for training purposes and for informing and/or warning caregivers.

In the foregoing embodiments an event relating to the dispensing of medicament is detected by means of movement of the index wheel 60 or by detection of scattered radiation by inhalation sensor 106. However, the detector can be provided by other means, based on events that are indicative of usage of the dispenser. These events include opening the cover 10, changes in flow rate and changes in pressure through the mouthpiece 36, so that other suitable detectors include a cover-movement detector and a pressure measuring device arranged to measure static and dynamic pressure (e.g. piezo electric crystal). In the case of the medicament dispenser being located in a holder until such time as medication is to be dispensed, removal of the dispenser could also be an event indicative of usage of the dispenser, in which case the detector can comprise a light emitter and detector pair located in the holder, which cooperatively provide a signal indicative of the presence, or removal, of the dispenser from the holder.

Whilst in the foregoing description the embodiments have been described as forming a part of a medicament dispenser, the alerting system (embodied in the control unit 90) could also be used in non-medicament contexts, since the alerting system essentially provides support for any events that involve usage of a device and that have to be performed on a regular basis, where the regularity is defined with respect to a previous event. For example, the alerting system could be used in conjunction with an electric toothbrush, where an action indicative of usage of a device comprises, e.g., removing the toothbrush from its holder.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the appended claims.

The invention claimed is:

1. An alerting system for use in generating an alert in respect of usage of a device relative to a prescribed regimen of usage of the device, the alerting system including a detector capable of detecting an event that is indicative of usage of the device and a display, the alerting system being arranged to invoke a selected alert state prior to the activation of a forthcoming said event by a user, the alert state being selectable from a plurality of different alert states, wherein each of the different alert states, when invoked, comprises a visual representation on the display, wherein each alert state represents a different stage of elapsed time since a previous said event, and wherein the alerting system is arranged to select an alert state in dependence on the elapsed time, wherein the different alert states comprise at least one first alert state which represents a stage of elapsed time where it is too early to use the device under the prescribed regimen, a second alert state which represents a stage of elapsed time where usage of the device is due under the prescribed regimen and at least one third alert state which represents a stage of elapsed time where usage of the device is overdue under the prescribed regimen, and wherein the visual representation of each alert state comprises a plurality of non-alphanumeric sub-regions, each sub-region representing a proportion of elapsed time within the stage to which the alert state corresponds.

2. An alerting system according to claim 1, wherein at least one alert state represents a length of time in excess of 2 hours.

3. An alerting system according to claim 1, wherein at least one alert state corresponds to a period that includes an elapsed time of 24 hours.

4. An alerting system according to claim 1, wherein at least one alert state corresponds to a period that includes an elapsed time in excess of 24 hours.

5. An alerting system according to claim 1, including at least two alert states, wherein the alert states include a first alert state corresponding to a period which includes an elapsed time of 24 hours and a second alert state corresponding to a period which includes an elapsed time of 12 hours.

6. An alerting system according to claim 1, wherein at least one alert state represents a different length of time to that represented by at least one of the other alert states or that represented by the other alert state.

7. An alerting system according to claim 1, wherein an alert state is visually distinct from each other alert state.

8. An alerting system according to claim 7, wherein each alert state has a different color, or configuration of colors, associated therewith.

9. An alerting system according to claim 1, wherein the alerting system is arranged to select an alert state in dependence on a relationship between the elapsed time and a time at which said forthcoming event is due.

10. An alerting system according to claim 9, wherein, in the event that the currently elapsed time is less than a specified amount of time before the time at which said forthcoming event is due, the alerting system is arranged to select an alert state that includes indicia indicative of inaction.

11. An alerting system according to claim 9, wherein, in the event that the currently elapsed time is within a specified amount of time from the time at which said forthcoming event is due, the alerting system is arranged to select an alert state that includes indicia indicative of action.

12. An alerting system according to claim 9, wherein, in the event that the currently elapsed time is greater than a specified amount of time after the time at which said forthcoming event is due, the alerting system is arranged to select an alert state that includes indicia indicative of action.

13. An alerting system according to claim 1, wherein the alerting system is operable to present the alert states at different alert rates, each alert rate representing a different stage of the elapsed time.

14. An alerting system according to claim 13, including at least one light emitting part operatively connected thereto.

15. An alerting system according to claim 13, including at least one sound emitting part operatively connected thereto.

16. An alerting system according to claim 1, wherein an alert state comprises a display mode having one or more regions each representing a different stage of the elapsed time.

17. An alerting system according to claim 16, wherein at least one region represents a different length of time to that represented by at least one of the other regions or that represented by the other region.

18. An alerting system according to claim 16, wherein at least one region represents the same length of time to that represented by at least one of the other regions or that represented by the other region.

19. An alerting system according to claim 1, including a sensor arranged to detect said event and a timer arranged to record elapsed time from the detected event.

20. An alerting system according claim 1, wherein the alerting system is arranged to select a default alert state in response to a newly detected event.

21. An alerting system according to claim 1, wherein the alerting system comprises a segmented display.

22. A medicament dispenser capable of detecting an event relating to the dispensing of medicament, comprising an alerting system according to claim 1.

23. A medicament dispenser according to claim 22, wherein the dispenser comprises an inhalation device adapted either for oral or nasal use.

24. A medicament dispenser capable of detecting an event relating to the dispensing of medicament relative to a prescribed regimen, wherein the dispenser is responsive to elapsed time since a previous said event, the dispenser comprising an alerting system arranged to invoke a selected alert state prior to the activation of a next said event by the user, the alert state being selectable from a plurality of different alert states, each of the different alert states, when invoked, comprises a visual representation on the display, wherein each alert state representing a different stage of elapsed time, wherein the dispenser is arranged to select an alert state in dependence on the elapsed time, wherein the different alert states comprise at least one first alert state which represents a stage of elapsed time where it is too early to use the device under the prescribed regimen, a second alert state which represents a stage of elapsed time where usage of the device is due under the prescribed regimen and at least one third alert state which represents a stage of elapsed time where usage of the device is overdue under the prescribed regimen, an wherein the visual representation of each alert state comprises a plurality of non-alphanumeric sub-regions, each sub-region representing a proportion of elapsed time within the stage to which the alert state corresponds.

* * * * *